United States Patent
Jenkins et al.

(10) Patent No.: US 6,328,569 B1
(45) Date of Patent: Dec. 11, 2001

(54) METHOD FOR TRAINING OF AUDITORY/VISUAL DISCRIMINATION USING TARGET AND FOIL PHONEMES/GRAPHEMES WITHIN AN ANIMATED STORY

(75) Inventors: William M. Jenkins, Pacifica; Michael M. Merzenich, San Francisco; Steven L. Miller, Pacifica; Bret E. Peterson, Lafayette, all of CA (US); Paula Tallal, Lumberville, PA (US)

(73) Assignee: Scientific Learning Corp., Oakland, CA (US)

( * ) Notice: Subject to any disclaimer, the term of this patent is extended or adjusted under 35 U.S.C. 154(b) by 0 days.

(21) Appl. No.: 09/105,916

(22) Filed: Jun. 26, 1998

Related U.S. Application Data

(63) Continuation-in-part of application No. 08/982,189, filed on Dec. 17, 1997, now Pat. No. 5,927,988.

(51) Int. Cl.[7] .................................................... G09B 5/00
(52) U.S. Cl. .................. 434/169; 434/167; 434/185; 434/307 R; 704/270; 704/503; 704/504; 706/16
(58) Field of Search ................................ 434/116, 118, 434/156, 157, 167, 169, 178, 185, 307 R, 308, 320, 322, 323, 362, 365; 704/1, 10, 200, 201, 211, 222, 231, 243, 251, 254, 257, 258, 260, 265, 266, 270, 270.1, 271, 503, 504; 706/16, 927; 345/473, 952, 956; 707/3, 5; 73/585; 600/559

(56) References Cited

U.S. PATENT DOCUMENTS

| | | | |
|---|---|---|---|
| 3,920,903 | * | 11/1975 | Beller ................................... 434/185 |
| 4,569,026 | * | 2/1986 | Best ..................................... 345/716 |
| 4,884,972 | * | 12/1989 | Gasper ................................. 434/185 |
| 4,907,274 | * | 3/1990 | Nomura et al. ........................ 380/30 |
| 5,170,432 | * | 12/1992 | Hackbarth et al. ................... 704/254 |
| 5,175,794 | * | 12/1992 | Tattersall ............................. 704/200 |
| 5,640,490 | * | 6/1997 | Hansen et al. ....................... 704/254 |
| 5,799,267 | * | 8/1998 | Siegel ..................................... 704/1 |
| 5,813,862 | * | 9/1998 | Merzenich et al. .................. 434/185 |
| 5,860,064 | * | 6/1999 | Henton ................................. 704/260 |
| 5,873,061 | * | 2/1999 | Häb-Umbach et al. ............. 704/254 |
| 6,026,361 | * | 2/2000 | Hura .................................... 704/270 |
| 6,036,496 | * | 3/2000 | Miller et al. ........................ 434/156 |
| 6,071,123 | * | 6/2000 | Tallal et al. ......................... 434/116 |
| 6,076,060 | * | 6/2000 | Lin et al. ............................. 704/260 |
| 6,078,885 | * | 6/2000 | Beutnagel ............................ 704/258 |
| 6,094,633 | * | 7/2000 | Gaved et al. ........................ 704/260 |
| 6,109,107 | * | 8/2000 | Wright et al. ......................... 73/585 |
| 6,234,802 | * | 5/2001 | Pella et al. ........................... 434/156 |

\* cited by examiner

*Primary Examiner*—Joe H. Cheng
(74) *Attorney, Agent, or Firm*—James W. Huffman

(57) ABSTRACT

A method for training of auditory and graphical discrimination in humans is provided within an animated game environment. The method provides a number of stimulus sets, each stimulus set having a target phoneme and a plurality of associated foils (similar sounding phonemes). Upon initiation of a trial, a target phoneme is presented to a subject. Subsequently, the target phoneme is presented to the subject, along with one of the associated foils, in randomized order. As the target phoneme and associated foil is presented, a graphical animation associates the target and foil each with its own graphical image. The subject then designates identification of the target phoneme by selecting its associated image. Speech processing is used to provide multiple levels of emphasis for enhancing the subject's ability to discriminate between the target phoneme and the foils. As a subject correctly identifies target phonemes, from their plurality of associated foils, the amount of processing applied to the target phonemes and foils is reduced, ultimately to the level of normal speech.

19 Claims, 12 Drawing Sheets

METHOD FOR TRAINING OF AUDITORY/VISUAL DISCRIMINATION USING TARGET AND FOIL PHONEMES/GRAPHEMES WITHIN AN ANIMATED STORY

This application is a Continuation-in-Part of co-pending U.S. patent application Ser. No. 08/982,189, filed Dec. 17, 1997, entitled "METHOD AND APPARATUS FOR TRAINING OF SENSORY AND PERCEPTUAL SYSTEMS IN LLI SUBJECTS", now U.S. Pat. No. 5,927,988; and is related to U.S. patent application Ser. No. 08/992,071, filed Dec. 17, 1997, entitled "METHOD AND APPARATUS FOR TRAINING OF SENSORY AND PERCEPTUAL SYSTEMS IN LLI SUBJECTS", now U.S. Pat. No. 6,019,607; and U.S. patent application Ser. No. 08/992,072, filed Dec. 17, 1997, entitled "METHOD AND APPARATUS FOR TRAINING OF COGNITIVE AND MEMORY SYSTEMS IN HUMANS", now U.S. Pat. No. 6,159,014, both assigned to Scientific Learning Corporation.

BACKGROUND OF THE INVENTION

1. Field of the Invention

This invention relates in general to the field of language education, and more specifically to a computer program for training a human's auditory processing system to discriminate between and accurately identify similarly sounding phonemes or words, and to associate representative graphemes with the phonemes or words.

2. Description of the Related Art

Up to ten percent of children have language-learning impairments (LLI) resulting from the inability to accurately process short duration acoustic events at the rates that occur in normal speech. Their trouble distinguishing among elements of speech is neurologically based and has far reaching consequences, including: academic failure, emotional and disciplinary problems, and possibly diminished lifelong achievement and self-image. No bracket of intelligence, race, gender or economic level is immune from this problem.

More specifically, Children with LLI have difficulty detecting and identifying sounds that occur simultaneously or in close proximity to each other—a phenomenon known as "masking." Because of masking, children with LLI require sounds that are as much as 45 decibels more intense than a preceding or subsequent masking noise to distinguish and understand them. In addition, children with LLI are consistently poorer at detecting a brief tone presented with a masking noise, particularly when the brief tone is turned on immediately prior to the masking noise. This phenomenon is called "backward masking." Similarly, when the brief tone is turned on immediately after the masking noise a similar decrease in detectability can occur. This phenomenon is called "forward masking". For a tone to be detected by a child with LLI in the presence of a masking noise, the tone must be separated in time or frequency from the masking noise.

The inability to accurately distinguish and process short duration sounds often causes children to fall behind in school. Since the children can't accurately interpret many language sounds, they can't remember which symbols represent which sounds. This deficiency causes difficulties in learning to read (translating from symbols to sounds), and in spelling. In fact, it is common for a child with LLI to fall two to three years behind his/her peers in speech, language and reading development.

One way children develop such auditory processing problems is from middle ear infections when they are young and beginning to develop the oral representations of language in the central auditory nervous system. When a child has an ear infection, fluid can build up and block or muffle the sound wave entering the ear causing intermittent hearing loss. Even if the infection doesn't permanently damage the ear, the child's brain doesn't learn to process some sounds because it hasn't heard them accurately before, on a consistent basis. This typically occurs during a critical period of brain development when the brain is building the nerve connections necessary to accurately process acoustic events associated with normal speech.

Researchers believe that the auditory processing problem is essentially one of timing. Vowel sounds like /a/ and /e/ usually last at least 100 milliseconds and typically have constant frequency content. Consonants, on the other hand, typically have modulated frequency components, and last less than 40 milliseconds. Children with LLI cannot process these faster speech elements, especially the hard consonants like /t/, /p/, /d/ and /b/, if they occur either immediately before or after vowels, or if they are located near other consonants. Rather than hearing the individual sounds that make up a particular phoneme, children with LLI integrate closely associated sounds together over time. Since the duration of vowels are typically longer than consonants, the modulated frequency portions of consonants are often lost in the integration, an affect that may also hinder the resolution of the vowel, particularly short duration vowels.

This problem of abnormal temporal integration of acoustic events over time is not limited to children with LLI. Rather, the problem extends to stroke victims who have lost the neurological connections necessary to process speech, as well as to individuals raised in one country, having one set of language phonemes, and attempting to learn the language of another country, having a distinct set of language phonemes. For example, it is known that an individual raised in Japan is not often presented with phonemes similar to the English r's and l's, because those consonants are not common in the Japanese language. Similarly, there are many subtleties in the sounds made by a speaker of Japanese that are difficult to distinguish unless raised in Japan. The phonetic differences between languages are distinctions that must be learned, and are often very difficult. But, they are clearly problems that relate to the temporal processing of short duration acoustic events.

The above described temporal processing deficiency has little if anything to do with intelligence. In fact, some LLI specialists argue that brains choosing this different route by which to absorb and reassemble bits of speech may actually stimulate creative intelligence, but at the expense of speech and reading problems.

Recent studies have shown that if the acoustic events associated with phonemes that are difficult to distinguish, such as /ba/ and /da/, are slowed down, or that the consonant portion of the phonemes are emphasized, that students diagnosed as LLI can accurately distinguish between the phonemes. In addition, if the interval between two complex sounds is lengthened, LLI students are better able to process the sounds distinctly.

Heretofore, the solution to the processing problem has been to place LLI students in extended special education and/or speech therapy training programs that focus on speech recognition and speech production. Or, more commonly, repetitive reading programs, phonic games, or other phonic programs are undertaken. These programs often last for years, with a success rate that is often more closely associated with the skill of the speech and language professional than with the program of study.

What is needed is a method and apparatus that allows a subject with abnormal temporal processing to train, or retrain their brain to recognize and distinguish short duration acoustic events that are common in speech. Moreover, what is needed is a program that repetitively trains a subject to distinguish phonemes at a normal rate, by emphasizing elements of speech to the point that they are distinguishable, or separating speech elements in time, and then adaptively adjusting the emphasis and separation of the speech elements to the level of normal speech. The adaptive adjustments should be made so as to encourage the subject to continue with the repetitions, and the number of repetitions should be sufficient to develop the necessary neurological connections for normal temporal processing of speech. Moreover, the program should provide acoustic signals to the brain that are better for phonetic training than normal human speech.

Furthermore, what is needed is a program that trains a subject to discriminate between similar phonemes in increasingly complex situations (i.e., identifying sounds at the beginning, middle and end of words), to identify sequences of stimuli that are delivered in rapid succession (i.e., at speeds common in normal speech), and to begin associating phonemes with particular graphic representations (graphemes).

SUMMARY

To address the above-detailed deficiencies, the present invention provides a method for adaptively training a human subject, within the context of an animated game, to distinguish between an auditorily presented target phoneme and a foil phoneme, and to associate the target phoneme with a corresponding grapheme, the method acoustically processing both the target and foil phonemes. The method includes: subsequent to presenting a processed target phoneme, presenting the processed target phoneme and its corresponding grapheme, and the processed foil phoneme and its corresponding grapheme, the target and foil phonemes presented in a randomized order. The method also includes detecting whether the subject indicated selection of the processed target phoneme, or the processed foil phoneme, and recording the selection. The method repeats presenting and detecting a predetermined number of times. After correct selection of a number of processed target phonemes by the subject, the method alters the processing applied to the target and foil phonemes.

In another aspect, the present invention provides a method for adaptively presenting a target phoneme to a subject, paired with one of a number of foil phonemes, the target and paired foil phoneme presented in a randomized order, the target and paired foil phonemes being acoustically processed to allow the subject to better distinguish between them. The method includes pairing the target phoneme with a first foil phoneme; presenting the paired phonemes to the subject for identification of the target phoneme; if the subject correctly identifies the target phoneme, pairing the target phoneme with a different foil; and repeating presentation of the paired phonemes.

In yet another aspect, the present invention provides a method for adaptively training a subject to distinguish between a target acoustic event that is common in spoken language, and a similar acoustic event, termed a foil, and to designate selection of the target acoustic event. The method utilizes a number of target acoustic events, each having an associated number of foils. The method includes playing one of the target acoustic events for the subject; pairing the target acoustic event with one of the foils; playing the target acoustic event with the paired foil; and if the subject designates selection of the target acoustic event, pairing the target acoustic event with a different foil, and repeating play of the target acoustic event and the paired foil.

BRIEF DESCRIPTION OF THE DRAWINGS

These and other objects, features, and advantages of the present invention will become better understood with regard to the following description, and accompanying drawings where:

FIG. 22 is a flow chart illustrating the adaptive training methodology incorporated into the game Treasure in the Tomb.

DETAILED DESCRIPTION

Figure 1:
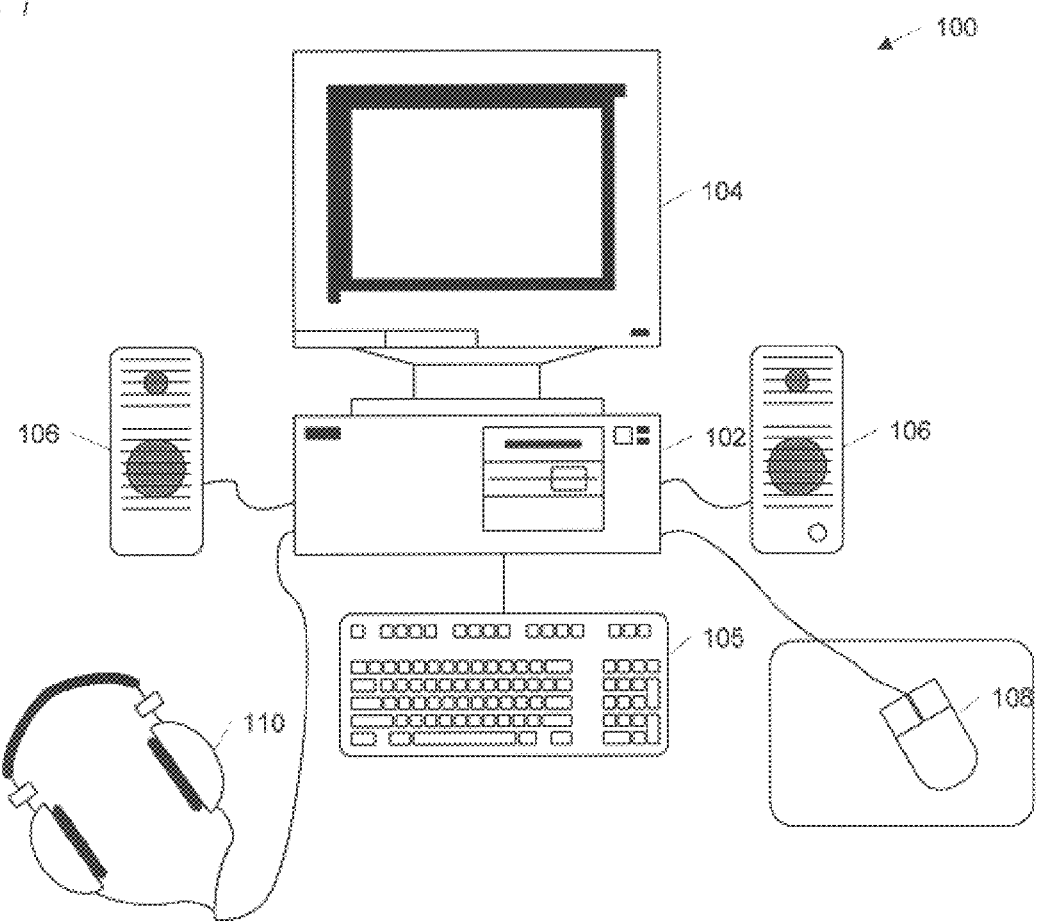
FIG. 1 is a block diagram of a computer system for executing a program according to the present invention.

Referring to FIG. 1, a computer system 100 is shown for executing a computer program to train, or retrain a subject, according to the present invention. The computer system 100 contains a computer 102, having a CPU, memory, hard disk and CD ROM drive (not shown), attached to a monitor 104. The monitor 104 provides visual prompting and feedback to the subject during execution of the computer program. Attached to the computer 102 are a keyboard 105, speakers 106, a mouse 108, and headphones 110. The speakers 106 and the headphones 110 provide auditory prompting and feedback to the subject during execution of the computer program. The mouse 108 allows the subject to navigate through the computer program, and to select particular responses after visual or auditory prompting by the computer program. The keyboard 105 allows an instructor to enter alpha numeric information about the subject into the computer 102. Although a number of different computer platforms are applicable to the present invention, embodiments of the present invention execute on either IBM compatible computers or Macintosh computers.

Figure 2:
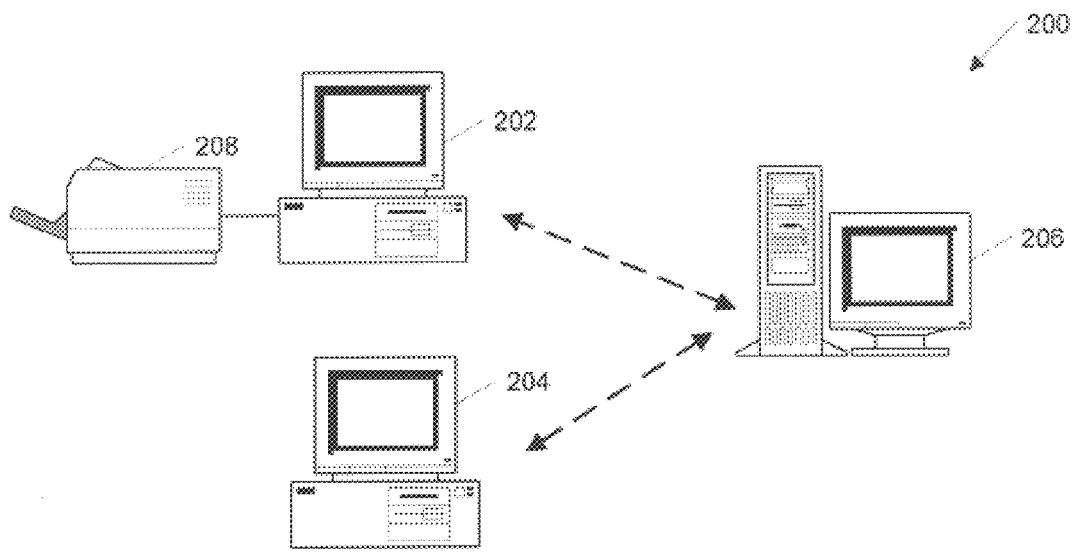
FIG. 2 is a block diagram of a computer network for executing a program according to the present invention.

Now referring to FIG. 2, a computer network 200 is shown. The computer network 200 contains computers 202, 204, similar to that described above with reference to FIG. 1 connected to a server 206. The connection between the computers 202, 204 and the server 206 can be made via a local area network (LAN), a wide area network (WAN), or via modem connections, directly or through the Internet. A printer 208 is shown connected to the computer 202 to illustrate that a subject can print out reports associated with the computer program of the present invention. The computer network 200 allows information such as test scores, game statistics, and other subject information to flow from a subject's computer 202, 204 to a server 206. An administrator can then review the information and can then download configuration and control information pertaining to a particular subject, back to the subject's computer 202, 204.

Before providing a detailed description of the present invention, a brief overview of certain components of speech will be provided, along with an explanation of how these components are processed by LLI subjects. Following the overview, general information on speech processing will be provided so that the reader will better appreciate the novel aspects of the present invention.

Figure 3:
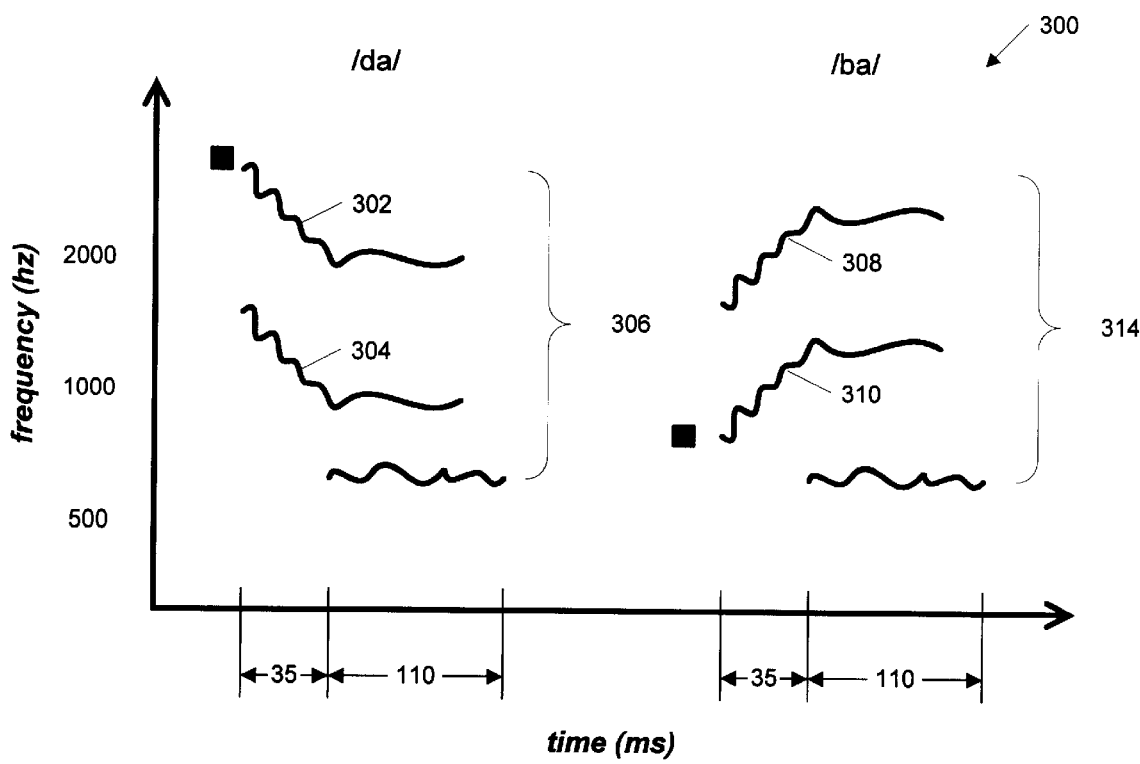
FIG. 3 is a chart illustrating frequency/energy characteristics of two phonemes within the English language.

Referring to FIG. 3, a chart is shown that illustrates frequency components, over time, for two distinct phonemes within the English language. Although different phoneme combinations are applicable to illustrate features of the present invention, the phonemes /da/ and /ba/ are shown. For the phoneme /da/, a downward sweep frequency component 302, at approximately 2.5–2 khz is shown to occur over a 35 ms interval. In addition, a downward sweep frequency component 304, at approximately 1 khz is shown to occur during the same 35 ms interval. At the end of the 35 ms interval, constant frequency components 306 are shown, whose duration is approximately 110 ms. Thus, in producing the phoneme /da/, the stop consonant portion of the element /d/ is generated, having high frequency sweeps of short duration, followed by a long vowel element /a/ of constant frequency.

Also shown are frequency components for a phoneme /ba/. This phoneme contains an upward sweep frequency component 308, at approximately 2 khz, having a duration of approximately 35 ms. The phoneme also contains an upward sweep frequency component 310, at approximately 1 khz, during the same 35 ms period. Following the stop consonant portion /b/ of the phoneme, are constant frequency vowel portions 314 whose duration is approximately 110 ms.

Thus, both the /ba/ and /da/ phonemes begin with stop consonants having modulated frequency components of relatively short duration, followed by a constant frequency vowel components of longer duration. The distinction between the phonemes exists primarily in the 2 khz sweeps during the initial 35 ms interval. Similarity exists between other stop consonants such as /ta/, /pa/, /ka/ and /ga/.

Figure 4:
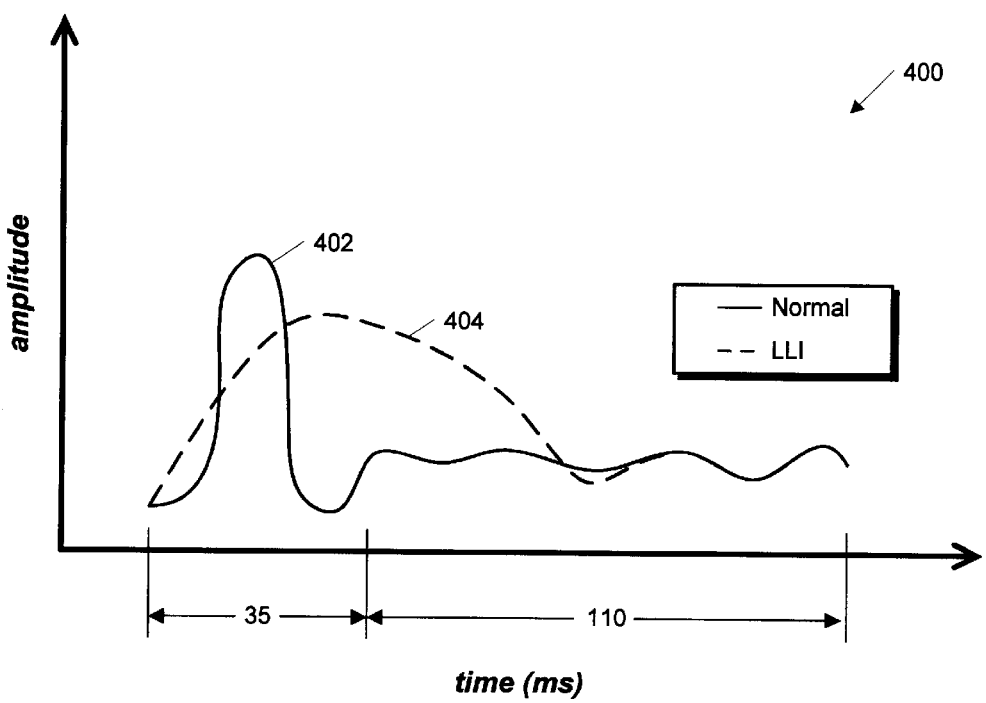
FIG. 4 is a chart illustrating auditory reception of a phoneme by a subject having normal receptive characteristics, and by a subject whose receptive processing is impaired.

Referring now to FIG. 4, the amplitude of a phoneme, for example /ba/, is viewed in the time domain. A short duration high amplitude peak waveform 402 is created upon release of either the lips or the tongue when speaking the consonant portion of the phoneme, that rapidly declines to a constant amplitude signal of longer duration. For an individual with normal temporal processing, the waveform 402 will be understood and processed essentially as it is. However, for an individual who is learning-language impaired, or who has abnormal temporal processing, the short duration, higher frequency consonant burst will be integrated over time with the lower frequency vowel, and depending on the degree of impairment, will be heard as the waveform 404. The result is that the information contained in the higher frequency sweeps associated with consonant differences, will be muddled, or indistinguishable.

With the above general background of speech elements, and how LLI subjects process them, a general overview of speech processing will now be provided. As mentioned above, one problem that exists in LLI subjects is the inability to distinguish between short duration acoustic events. If the duration of these acoustic events is stretched, in the time domain, it is possible to train LLI subjects to distinguish between these acoustic events. An example of such time domain stretching is shown in FIG. 5, to which attention is now directed.

Figure 5:
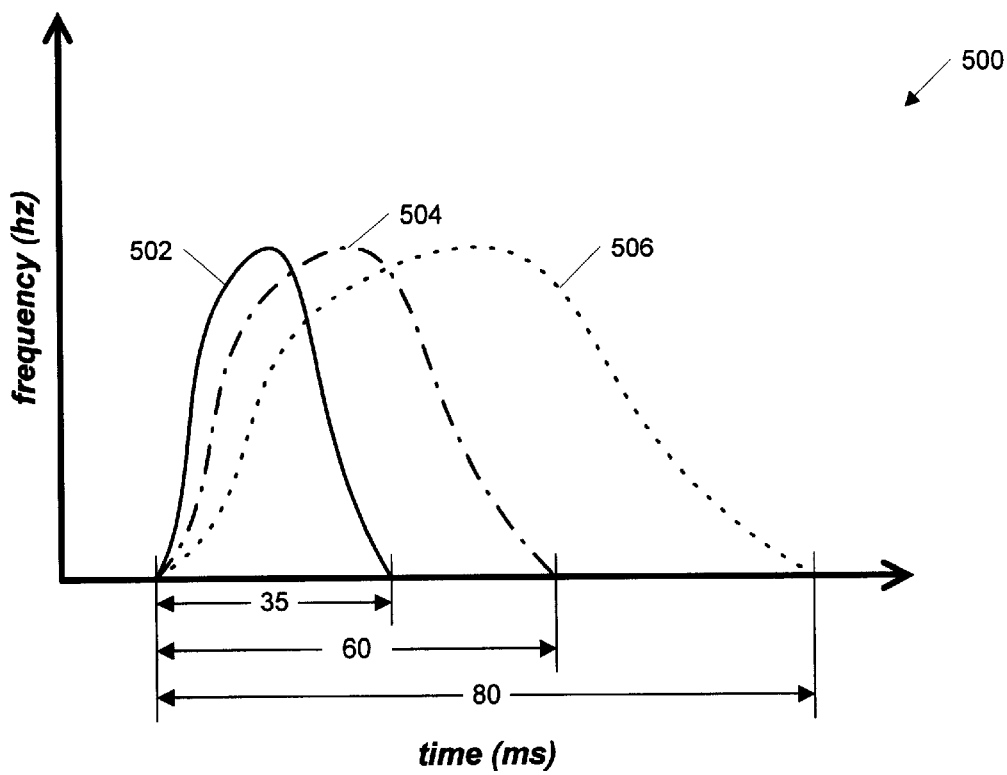
FIG. 5 is a chart illustrating stretching of a frequency envelope in time, according to the present invention.

In FIG. 5, a frequency vs. time graph 500 is shown that illustrates a waveform 502 having short duration characteristics similar to the waveform 402 described above. Using existing computer technology, the analog waveform 502 can be sampled and converted into digital values. The values can then be manipulated so as to stretch the waveform in the time domain to a predetermined length, while preserving the amplitude and frequency components of the modified waveform. The modified waveform can then be converted back into an analog waveform for reproduction by a computer, or by some other audio device. The waveform 502 is shown stretched in the time domain to durations of 60 ms (waveform 504), and 80 ms (waveform 506). By stretching the consonant portion of the waveform 502 without effecting its frequency components, subjects with LLI can begin to hear distinctions in common phonemes.

Figure 6:
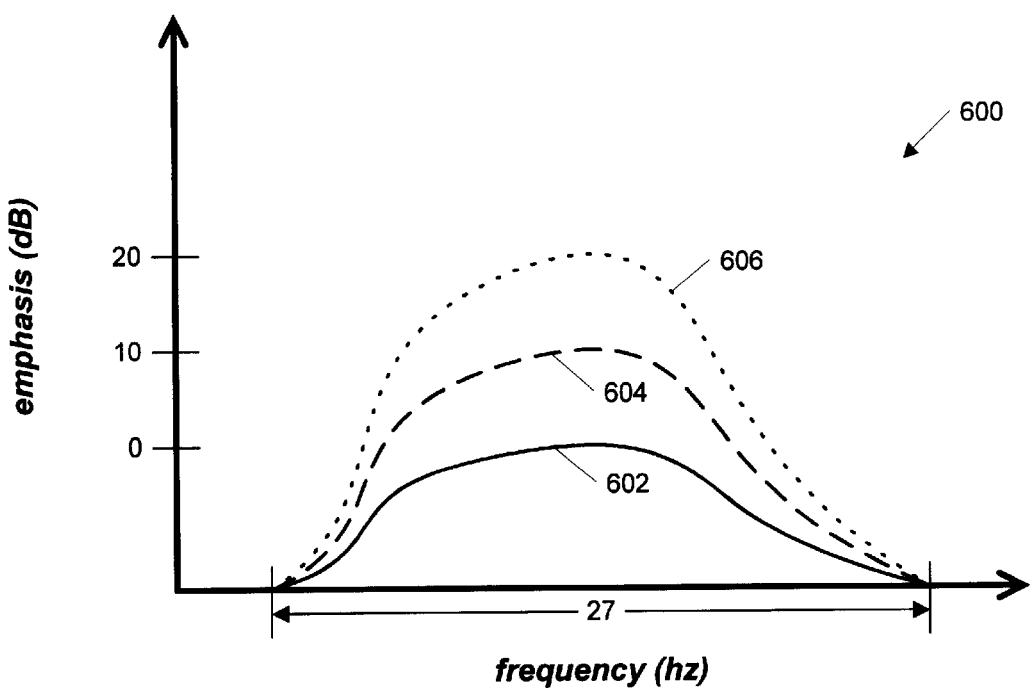
FIG. 6 is a chart illustrating emphasis of selected frequency components, according to the present invention.

Another method that may be used to help LLI subjects distinguish between phonemes is to emphasize selected frequency envelopes within a phoneme. Referring to FIG. 6, a graph 600 is shown illustrating a frequency envelope 602 whose envelope varies by approximately 27 hz. By detecting frequency modulated envelopes that vary from say 3–30 hz, similar to frequency variations in the consonant portion of phonemes, and selectively emphasizing those envelopes, they are made more easily detectable by LLI subjects. A 10 dB emphasis of the envelope 602 is shown in waveform 604, and a 20 dB emphasis in the waveform 606.

Figure 7:
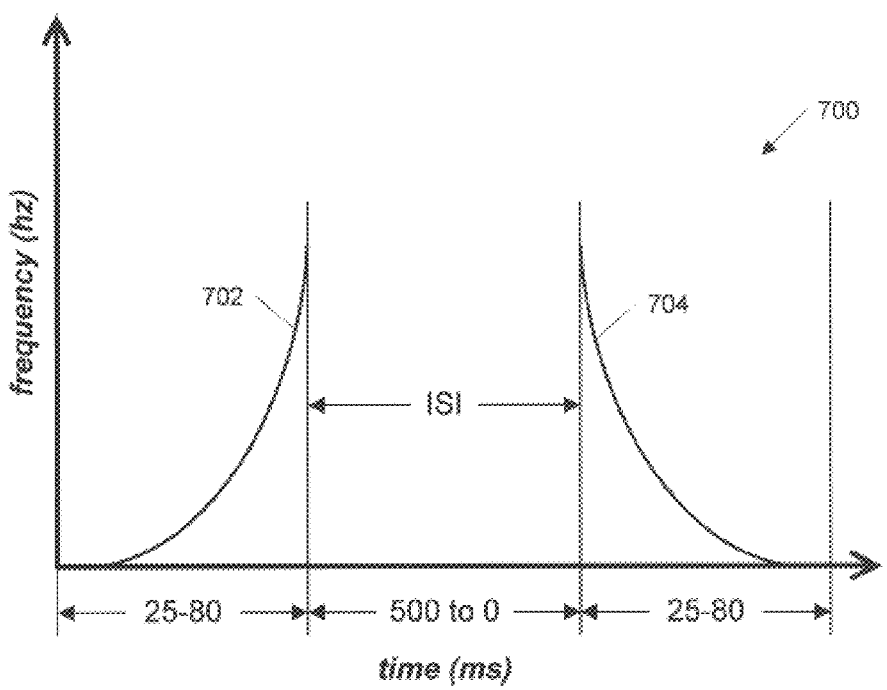
FIG. 7 is a chart illustrating up-down frequency sweeps of varying duration, separated by a selectable inter-stimulus-interval (ISI), according to the present invention.

A third method that may be used to train LLI subjects to distinguish short duration acoustic events is to provide frequency sweeps of varying duration, separated by a predetermined interval, as shown in FIG. 7. More specifically, an upward frequency sweep 702, and a downward frequency sweep 704 are shown, having duration's varying between 25 and 80 milliseconds, and separated by an inter-stimulus interval (ISI) of between 500 and 0 milliseconds. The duration and frequency of the sweeps, and the inter-stimulus interval between the sweeps are varied depending on the processing level of the LLI subject, as will be further described below.

Utilization of up-down frequency sweeps with varying ISI has been fully described in U.S. patent application Ser. No. 08/858961, entitled "METHOD AND DEVICE FOR ENHANCING THE RECOGNITION OF SPEECH AMONG SPEECH-IMPAIRED INDIVIDUALS", and is hereby incorporated by reference.

The above described methods have been combined in a unique fashion by the present invention to provide an adaptive training method and apparatus for training subjects having abnormal temporal processing abilities to recognize and distinguish short duration acoustic events that are common in speech. More specifically, emphasis has been used to intensify format transitions of stop consonants that are presented to a subject. It is believed that the differential gain of critical acoustic components generates more vigorous neural activity, which leads to better signal differentiation by neural networks involved in speech perception.

The present invention is embodied into a computer program entitled Fast ForWord II by Scientific Learning Corporation. The computer program is provided to an LLI subject via a CD-ROM that is input into a general purpose computer such as that described above with reference to FIG. 1. In addition, a user may log onto a server, via an Internet connection, for example, to upload test results, and to download training parameters for future exercises. Specifics of the present invention will now be described with reference to FIGS. 8–22.

Figure 8:
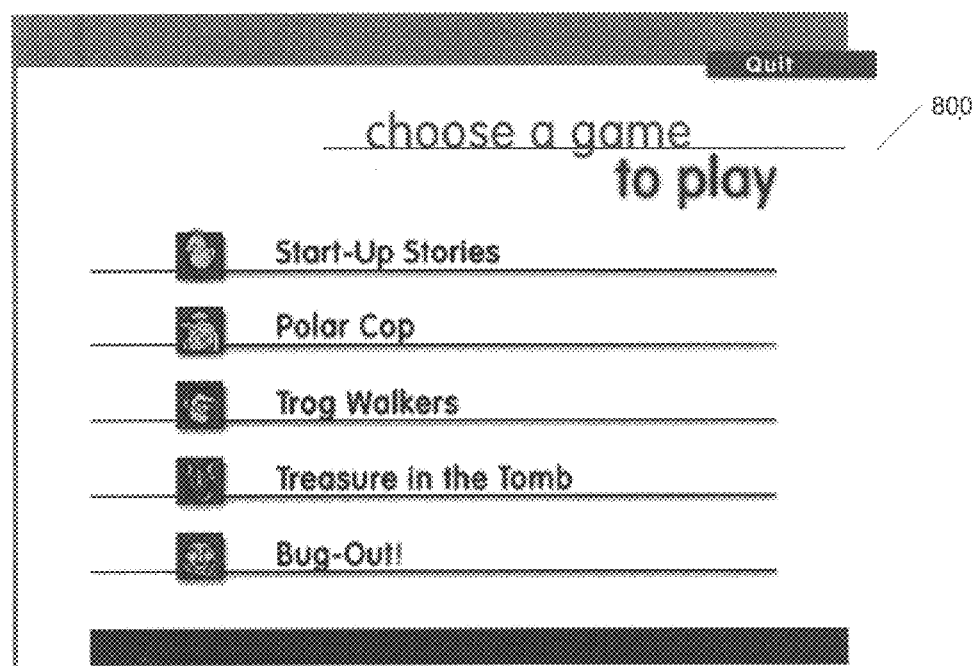
FIG. 8 is a pictorial representation of a game selection screen according to the present invention.

Referring first to FIG. 8, a pictorial representation is shown of a game selection screen 800. The game selection screen 800 is similar to that provided to a subject upon initialization of the computer program according to the present invention. The game selection screen 800 includes the titles of five computer games that provide distinct training exercises for improving language recognition in subjects who abnormally process temporal acoustic events, and for building, or rebuilding the neurological connections necessary to accurately process phonemes at the rates common in speech. The game titles include: 1) Start-Up Stories; 2) Polar Cop; 3) Trog Walkers; 4) Treasure in the Tomb; and 5) Bug-Out!.

When a subject begins execution of the Fast ForWord II computer program, he/she is presented with a screen similar to the screen 800. More specifically, upon initiation of the program, the subject is presented with a screen that lists the subjects that are currently being trained by the program. The subject, or instructor, then selects his/her name from the list. Once the subject has selected his/her name, a screen similar to 800 appears, typically listing the five programs, according to a training schedule that is dictated by the program, or is modified by an instructor. The order of the games that is presented in the screen 800 may vary from day to day, depending on which games the subject has previously played. In addition, after a subject has completed play of a particular game, that game may be shown "grayed out", indicating that it may not be selected again that day unless all other scheduled exercises have already been played. The subject then selects to play one of the games listed.

In one embodiment, a training schedule is provided by a certified Speech and Language Professional (SLP), and the SLP oversees each training session according to the schedule. An exemplary schedule requires a subject to cycle through the games for an hour and forty minutes, five days per week, for approximately six weeks.

In an alternative embodiment, the game schedule is specified by an SLP at a remote server, and the daily parameters of the schedule are downloaded to the subject's computer, either daily or weekly. The schedule can be optimized over the course of the training program according to the performance or skill of the subject. It can also be used to help manage time in each game so that all of the games are completed in about the same time at the end of the training program. This can be accomplished by an automated computer algorithm that adjusts the time allotted for each training exercise. This algorithm is individually adaptive and can adjust the times for each exercise on an individual subject basis using performance and estimates of time to complete the entire training sequence. This embodiment allows a subject to obtain the benefits of the Fast ForWord II program, and the oversight of a certified SLP, regardless of his/her geographic location. One skilled in the art will appreciate that the training schedule could either be provided in a window on the subject's computer, or could actually control the game selection screen to prompt the user only for those games required on a particular day.

Once a subject selects a particular game, he/she is taken into that particular game's module. Alternatively, once the subject selects his/her name from the list, the particular games may be presented, in a predefined order, without requiring the subject to first select the game.

The present application provides a detailed description of the game "Treasure in the Tomb". The other games shown in FIG. 8 are described in co-pending U.S. Patent Application: to U.S. Pat. No. 6,190,173; U.S. Pat. No. 6,210,166; U.S. application Ser. No. 09/106,939; and U.S. application Ser. No. 09/106,947, which are hereby incorporated by reference.

Treasure in the Tomb is a game that adaptively trains a subject to distinguish between similarly sounding phonemes and to associate phonemes with their graphemes. Phonemes include consonant (C), consonant-vowel-consonant (CVC), and consonant-vowel-consonant-consonant (CVCC) constructs. The game presents a series of trials that provide target phonemes of processed speech to the subject for identification. As the subject accurately identifies the target phonemes from a similar sounding phoneme (foil), the amount of processing applied to the phonemes is reduced, ultimately to the level of normal speech. The trials are placed within a game environment to entertain and amuse the subject so that multiple iterations are considered enjoyable rather than tedious. For purposes of the present invention, the terms "phoneme" and "word" are used interchangeably, to designate particular aural events that must be perceived by a subject.

The premise of Treasure in the Tomb is as follows. The game begins in the desert in modern day Egypt. The subject has to uncover the hidden entrance to an old temple buried deep in the sand. Once the temple is uncovered, the subject must advance through the temple, through secret chambers, mazes, etc. as will be further described below, to find pharaoh Phonemes death chamber and his treasure. The game maintains the subject's interest by moving the subject through different scenes, each uncovering bits and pieces of treasure along the way.

A complete description of the trial methodology used by Treasure in the Tomb, as well as the phonemes tested, and the adaptive nature of the game, will be provided below with reference to FIG. 21. However, to better appreciate the methodology used within Treasure in the Tomb, an overview of the game will first be provided, with reference to several screens within the game.

Figure 9:
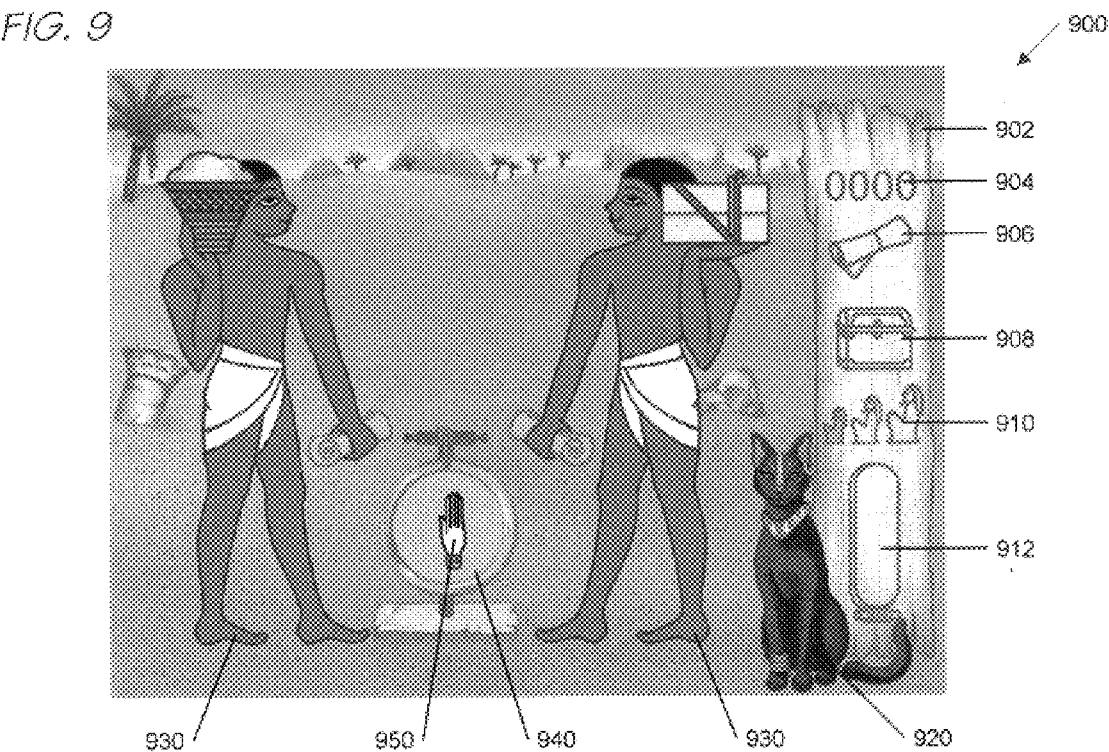
FIG. 9 is a pictorial representation of an initial game screen for a game entitled "Treasure in the Tomb" according to the present invention.

Referring to FIG. 9, a screen 900 is shown with a papyrus 902 that contains all the common game and game specific elements. These include: the subject's score 904, a map icon 906, a treasure chest 908, processing level icons 910 and a cartouche 912.

The map icon 906 works as a progress indicator, to show how far the subject is in the game. At the beginning of the game, the map is just a black and white drawing. Every scene the subject completes shows up colored in on the map. The map is active and available for viewing in the last two minutes of game play. Once the map has been viewed, closing it will deactivate the map from further viewing in the same play session.

The treasure chest 908 stores all the coins, nuggets, and other treasures that the subject "finds" during the game. Once a treasure is discovered, it automatically goes into the treasure chest 908, without any interaction by the subject.

The processing level icons 910 indicate which of 3 processing levels the subject is currently being used for the trials. As will be further described below, the 3 processing levels used are: 1) 20 db emphasis; 2) 10 db emphasis; and 3) 0 db emphasis (i.e., normal speech).

The cartouche 912 is a hieroglyphic combination that the subject must know to enter the tomb of pharaoh phoneme. As the subject progresses through the game scenes, s/he will find hieroglyphs in the form of a piece of jewelry. Once they are discovered, they will automatically appear in the cartouche 912. When the subject reaches the final scene, s/he must enter the hieroglyphic combination to unlock the door of the tomb.

Also within the screen 900 is a cat 920. The cat 920, called Nefertari, acts as a helper to the subject. At the beginning of a training session, the cat 920 welcomes the subject, explains every scene to the subject, and provides positive encouragement to the subject during training. To make the game more interesting, the cat 920 performs a number of animations, including digging in the sand to locate the tomb.

A pair of stimulus characters 930 appears in each scene. The characters 930 are restricted to 3 positions: 1) a still position, as shown in FIG. 9; 2) a mouth open position, when speaking a phoneme; and 3) a scroll open position, when illustrating the grapheme associated with a spoken phoneme.

Finally, a trial initiation button is provided in the form of a gong 940. In one embodiment, the subject initiates a trial by moving a cursor 950 (in the form of a hand) over the gong 940, and signaling selection, by pressing a button on a computer mouse, for example. When the gong 940 is selected, the game presents an auditory phoneme to the subject, via headphones or speakers attached to a computer.

Figure 10:
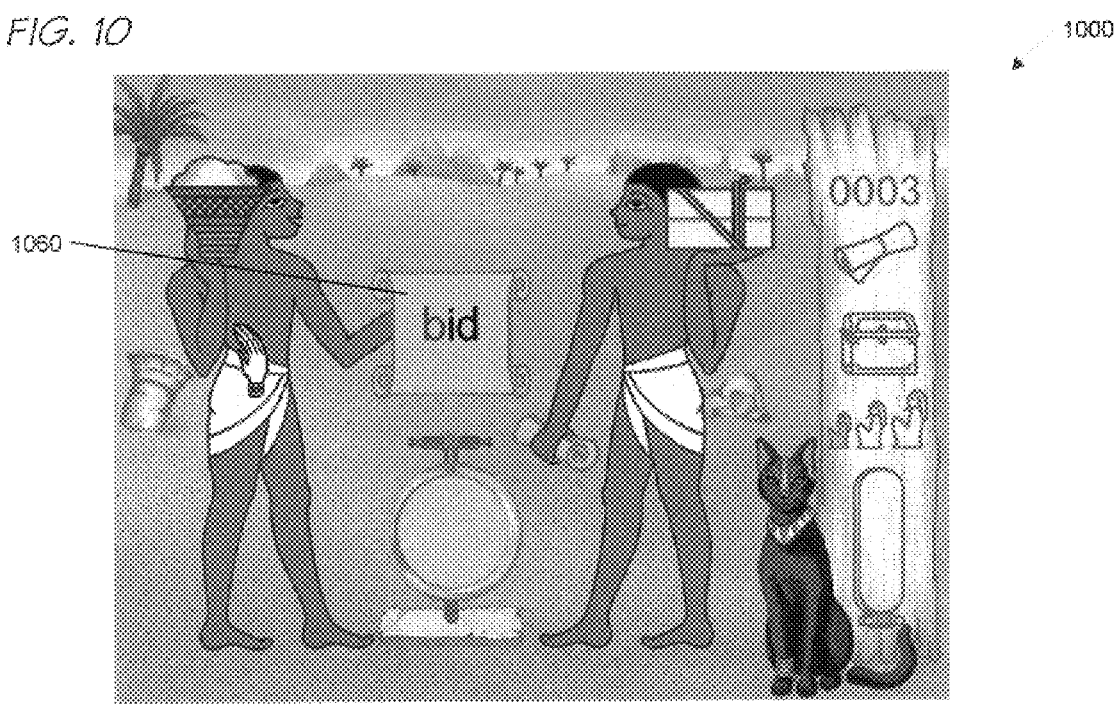
FIG. 10 is a pictorial representation of a game screen in Treasure in the Tomb illustrating presentation of a phoneme "bid".

The auditorily presented phoneme is termed the "target" phoneme, because it is the phoneme that must be identified within a subsequently presented sequence. In one embodiment, the subsequently presented sequence presents the target phoneme, and a foil, in random order. A foil is a phoneme that looks and sounds similar to the target phoneme. As will be further explained below, for each target phoneme that is tested, a number of different foils are provided. In the case of the target phoneme "bid", the foils include: "did", "kid", and "lid". The subject must then distinguish between the target phoneme and the foil, and indicate selection of the target phoneme. Referring now to FIG. 10, a screen 1000 is shown that includes all of the elements listed in FIG. 9. In addition, one of the stimulus characters 930 is shown presenting a grapheme 1060. The grapheme 1060 is presented in parallel with presentation of an associated phoneme. That is, in addition to presenting a grapheme 1060, the stimulus character 930 also speaks an associated phoneme. The phoneme/grapheme 1060 presented is either the target phoneme or a foil. In one embodiment, the stimulus character 930 on the left of the screen presents his phoneme/grapheme 1060, and then the stimulus character 930 on the right presents his phoneme/grapheme. If the stimulus character 930 on the left presents the target phoneme, the stimulus character 930 on the right will present a foil. If the stimulus character 930 on the left presents a foil, the stimulus character 930 on the right will present the target phoneme.

Within the grapheme 1060, the particular consonant that is being tested is highlighted in a color different from the other letters in the phoneme. For example, in the scene 1000, the first letter "b" is shown in a color different from the letters "id". This provides a visual clue to the subject regarding what s/he is being tested on in the trial.

Figure 11:
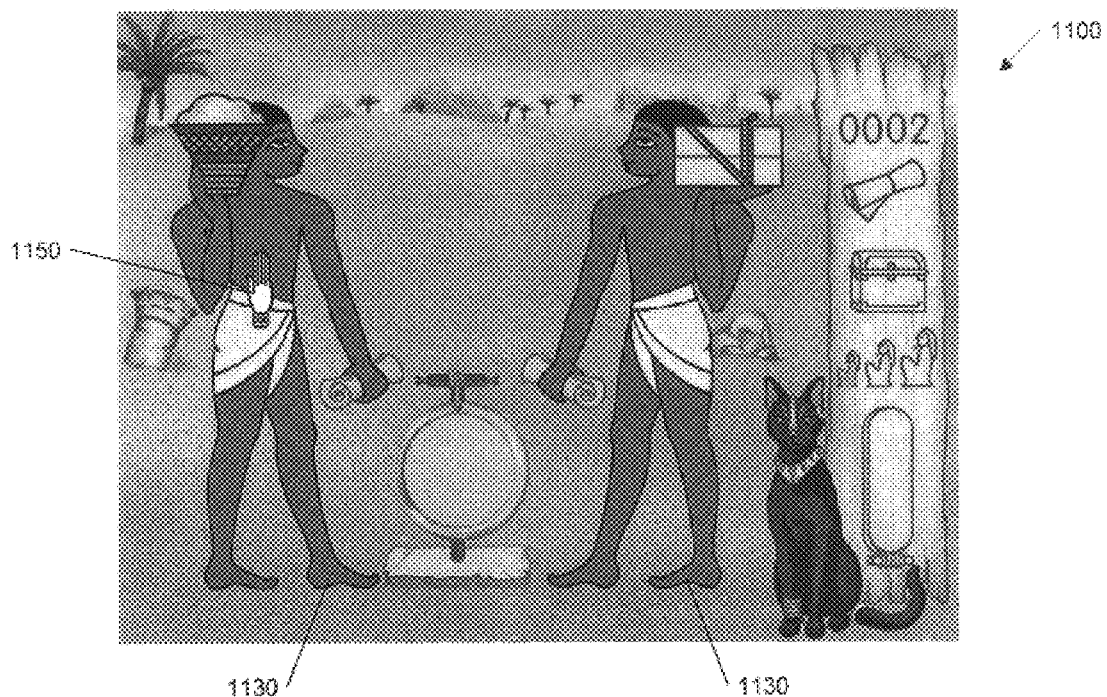
FIG. 11 is a pictorial representation of a game screen in Treasure in the Tomb illustrating selection of a character associated with the phoneme "bid" of FIG. 10.

Referring now to FIG. 11, a screen 1100 is shown. The screen 1100 includes all of the elements described above in FIG. 9. It should be appreciated that the grapheme 1060 is no longer shown within the screen 1100. This is because both of the stimulus characters 1130 have presented their phoneme/grapheme. At this point, the subject must select which of the characters 1130 presented the target phoneme. The subject indicates his selection by moving the cursor 1150 on top of the stimulus character 1130 that s/he believes presented the target phoneme, and selecting the character 1130. In one embodiment, selection is made by pressing a button on a computer mouse.

Figure 12:
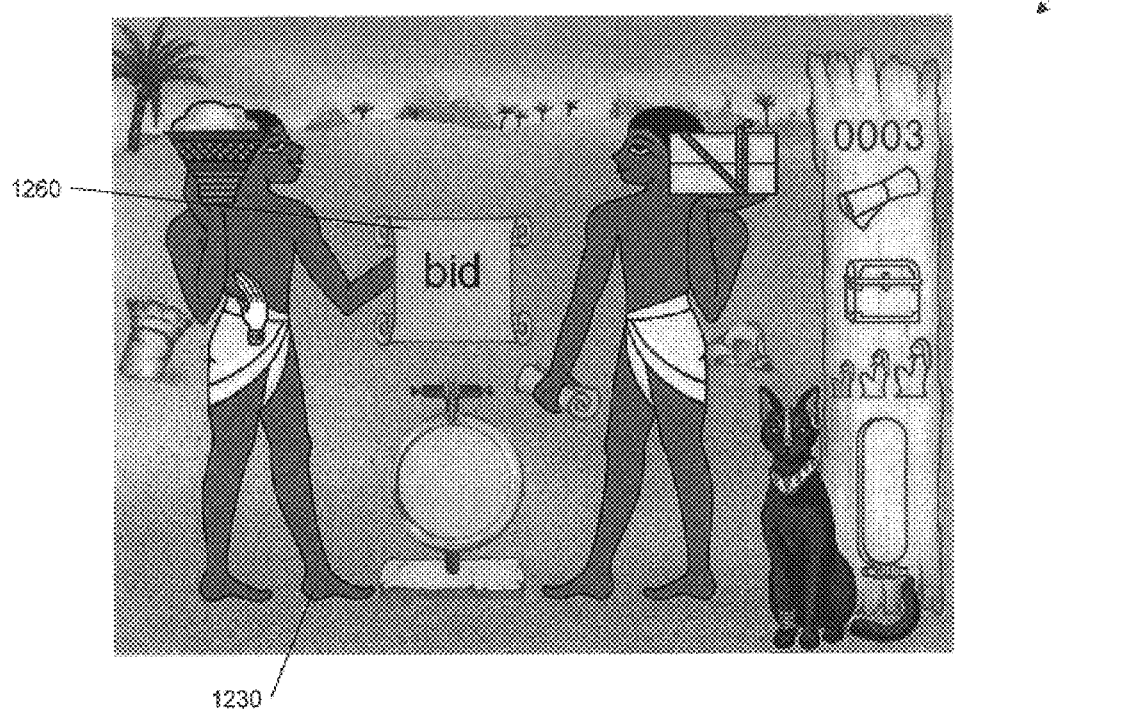
FIG. 12 is a pictorial representation of a game screen in Treasure in the Tomb illustrating presentation of a foil phoneme "lid" in the context of a trial with a target phoneme of "bid".
Figure 13:
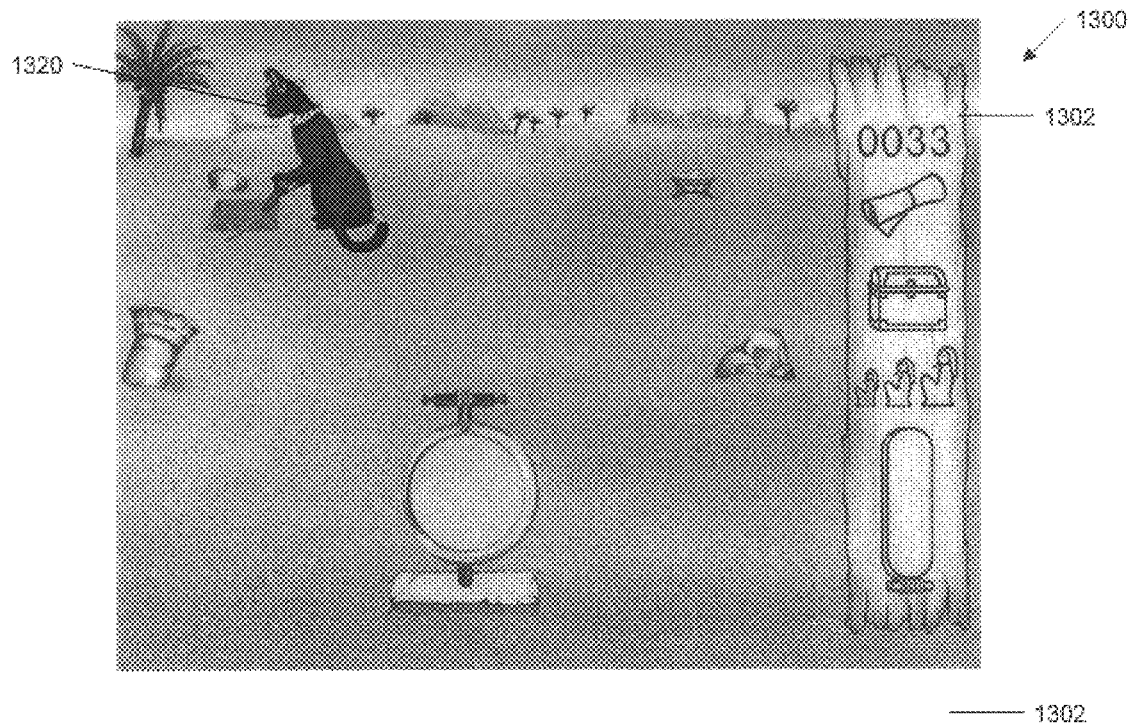
FIG. 13 is a pictorial representation of a game screen in Treasure in the Tomb illustrating a reward animation.

Referring now to FIG. 12, if the subject correctly identifies the stimulus character 1230 that presented the target phoneme, the target phoneme, and its associated grapheme 1260, are again presented to the subject. Otherwise, no grapheme presentation is made, and the subject's incorrect selection is responded to by an auditory "thunk". Referring now to FIG. 13, a screen 1300 is presented illustrating a reward animation. A reward animation is a graphical movie type animation that is presented to the subject after a predetermined number of correct responses, or after a predetermined time period. The animation unfolds the story of the game as the subject proceeds through the trials. In screen 1300, the cat 1320 is shown digging in the sand. In one embodiment of the present invention, the cat 1320 digs two shovels full of sand and then returns to sit next to the papyrus 1302. After another set of completed trials, or elapse of another time period, the cat 1320 will perform further excavation. The reward animations have been designed to engage the interest of the subject, and to provide motivation for the subject to continue playing the game, and to respond correctly to as many trials as possible. Once the reward animation is completed, game play returns to a scene similar to that shown above in FIGS. 9–12.

Figure 14:
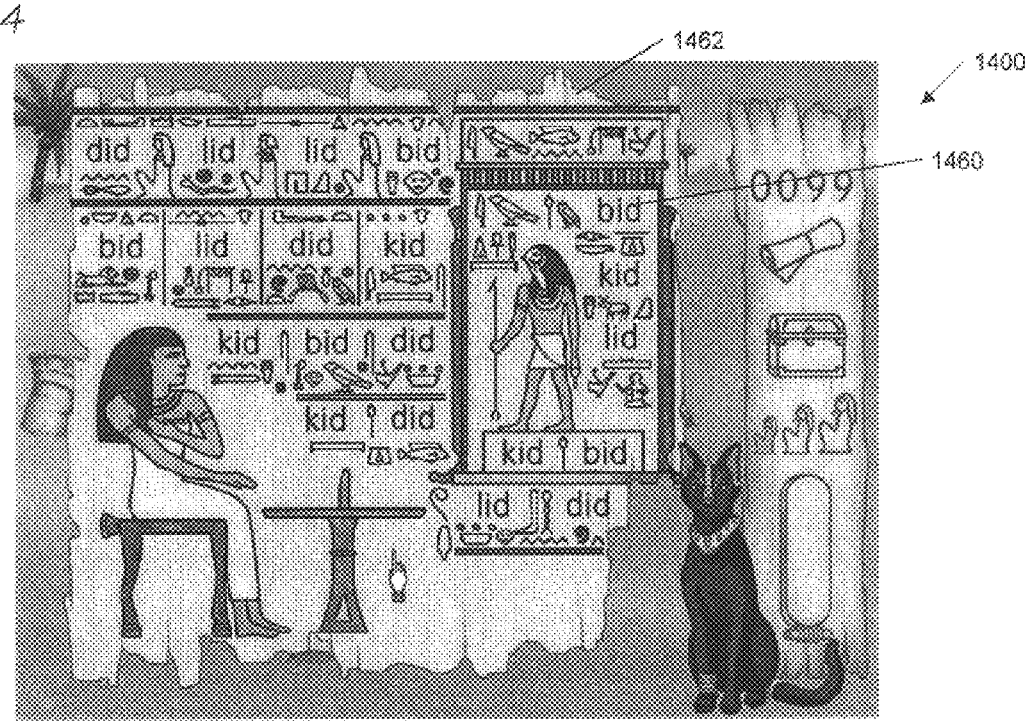
FIG. 14 is a pictorial representation of a game screen in Treasure in the Tomb illustrating a bonus game play.

Referring now to FIG. 14, a screen 1400 is shown of a bonus game play. The bonus game play is provided to a subject at the end of each game session. The bonus game play offers the subject the possibility of earning extra points by finding graphemes 1460 on a special papyrus 1462. All target phonemes (and foils) presented to the subject on particular day of game play are included within the bonus game play. That is, graphemes 1460 of target and foil phonemes are incorporated into the papyrus 1462. In the bonus game play, the subject is to find as many of the target graphemes as possible. In one embodiment, a target phoneme is auditorily presented to the subject. The subject must then identify its corresponding grapheme, in as many places as it is found on the papyrus 1462. If the subject guesses incorrectly three times, the bonus game play is over, and game play returns to the screen 900. The bonus game play continues for two minutes, allowing the subject to accumulate points for every correct grapheme identified.

Figure 15:
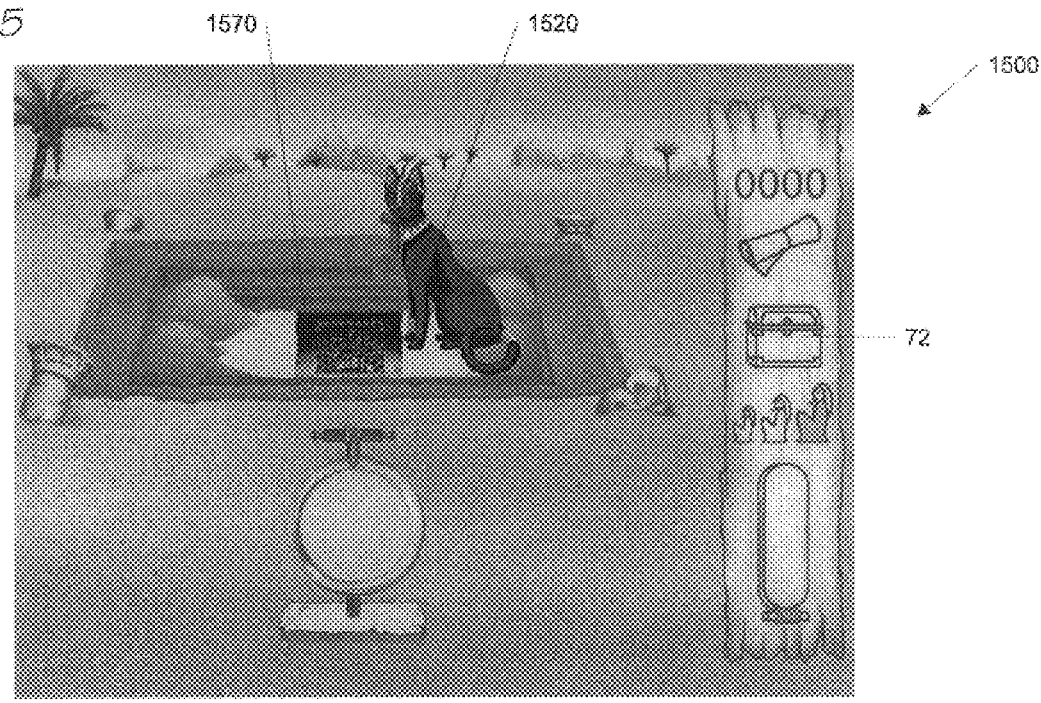
FIG. 15 is pictorial representation of a game screen in Treasure in the Tomb illustrating selection of target phonemes (words) within the bonus game play of FIG. 14.

Referring now to FIG. 15, a screen 1500 is shown. The screen 1500 shows the cat 1520 uncovering the entrance to a hidden temple 1570. As explained above, after a predetermined number of trials, the cat 1520 will start digging in the sand. Within each reward animation, the cat 1520 will progress two shovels full. As the cat 1520 digs, she uncovers a number of treasures that are hidden in the sand. The treasures, when uncovered, automatically are moved into the treasure chest 1508. As further animations are played, the cat 1520 eventually discovers the entrance to the temple 1570.

Figure 16:
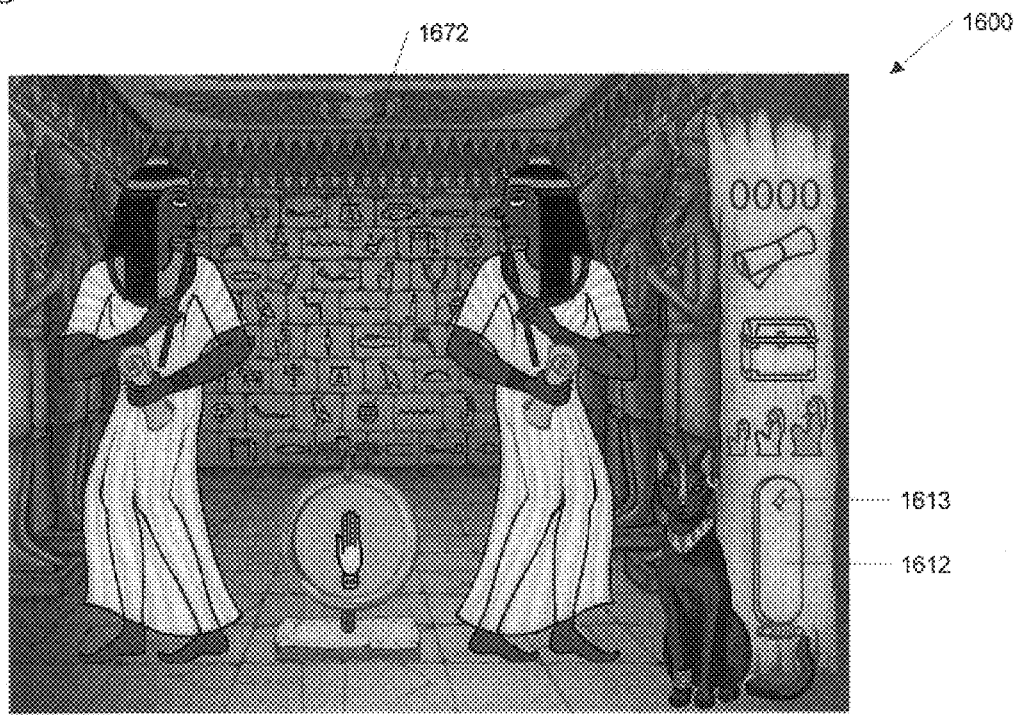
FIG. 16 is a pictorial representation of a screen in Treasure in the Tomb illustrating an additional reward play, according to the story line of the game.

Referring now to FIG. 16, a screen 1600 of the first hall within the temple is shown. The screen 1600 contains all of the elements listed above in FIG. 9. However, the setting of the game play is now within the hidden temple. In addition, the cartouche 1612 is shown with a first hieroglyphic 1613, indicating the subject's progress through the game. In one embodiment, the subject reaches pharaoh phoneme's tomb when 4 hieroglyphics are shown on the cartouche 1612.

The first hall of the temple is shown sealed off by a wall of stone blocks 1672 with hieroglyphics on them. Similar to the reward animations described above, as the subject progresses through a predetermined number of trials, reward animations are played that remove the stones 1672, one at a time. Initially, the stones 1672 are shown faint in color. However, when a reward animation plays, the stones 1672 colorize, and are then moved away.

Figure 17:
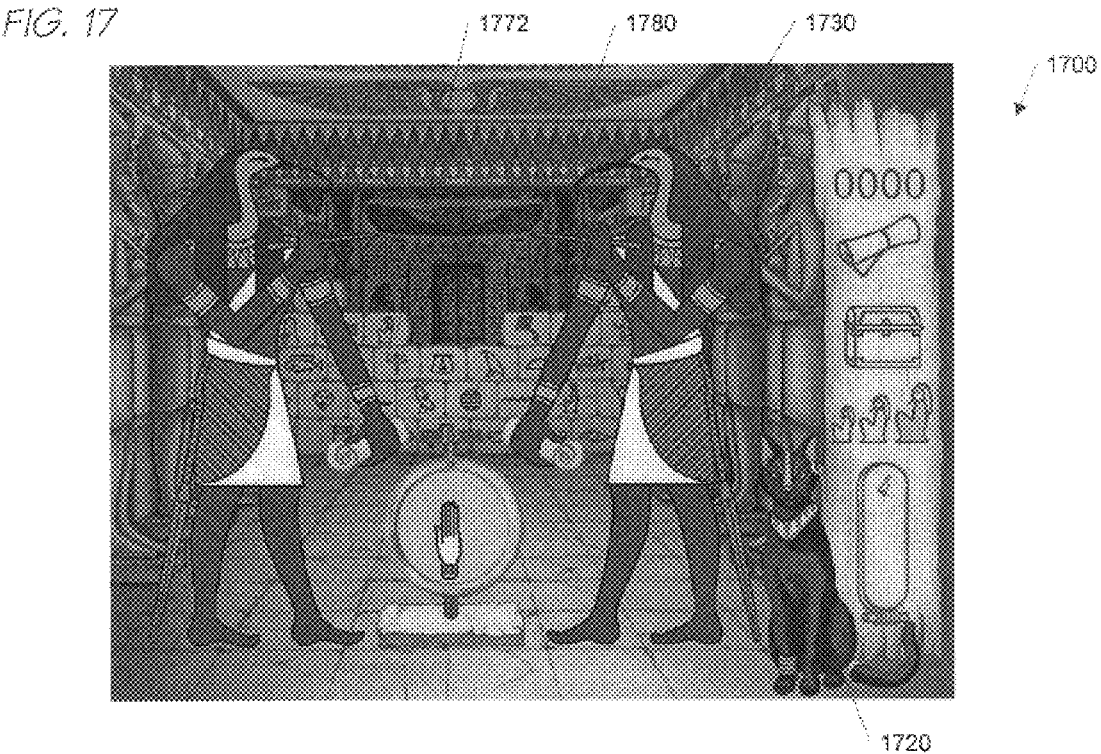
FIG. 17 is a pictorial representation of a screen in Treasure in the Tomb illustrating another game scene within the game.

Referring now to FIG. 17, a screen 1700 is shown illustrating the first hall of the temple, with a number of the stones 1772 removed. Behind the stones 1772 is an entrance room 1780 to a maze. The entrance room 1780 is the next scene into which the subject is to progress. When the opening in the stones 1772 is complete, the cat 1720 will walk through into the room 1780. Also shown is an alternate pair of stimulus characters 1730. In each scene, a plurality of stimulus characters are provided, that are alternated as the subject completes a particular target/foil set.

Figure 18:
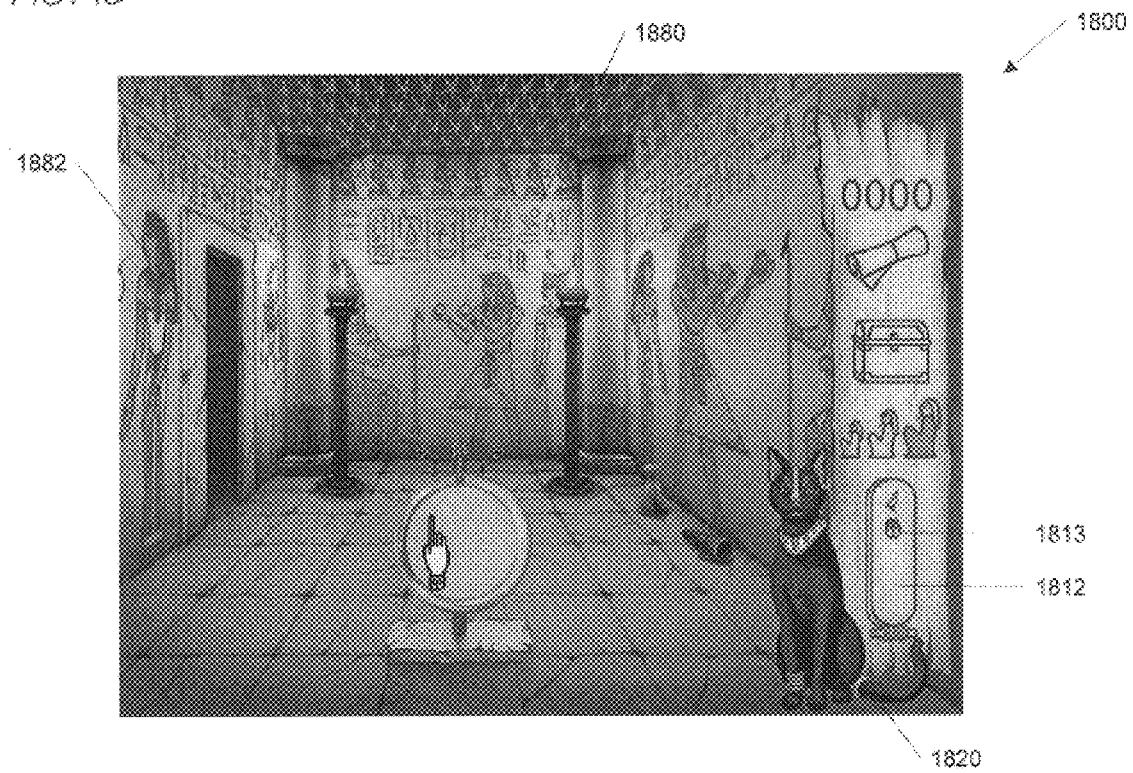
FIG. 18 is a pictorial representation of a screen in Treasure in the Tomb illustrating progression through the game scene of FIG. 17.

Referring now to FIG. 18, a screen 1800 is shown of the entrance room 1880 to the maze. The entrance room 1880 contains a door 1882 (or a set of doors, not shown) through which the subject must progress to get to the next scene. When the subject first enters the room 1880, all of the doors are closed. As before, when the subject correctly completes a predetermined number of correct trials, the door 1882 (or doors) will open. The subject then selects a door 1882, and upon selection, the cat 1820 walks through, taking the subject into the maze. Eventually, the last door in the maze will open, taking the subject into pharaoh phoneme's treasure room. It should be noted that upon entering the maze entrance room 1880, the cartouche 1812 is updated to reflect an additional hieroglyphic 1813.

Figure 19:
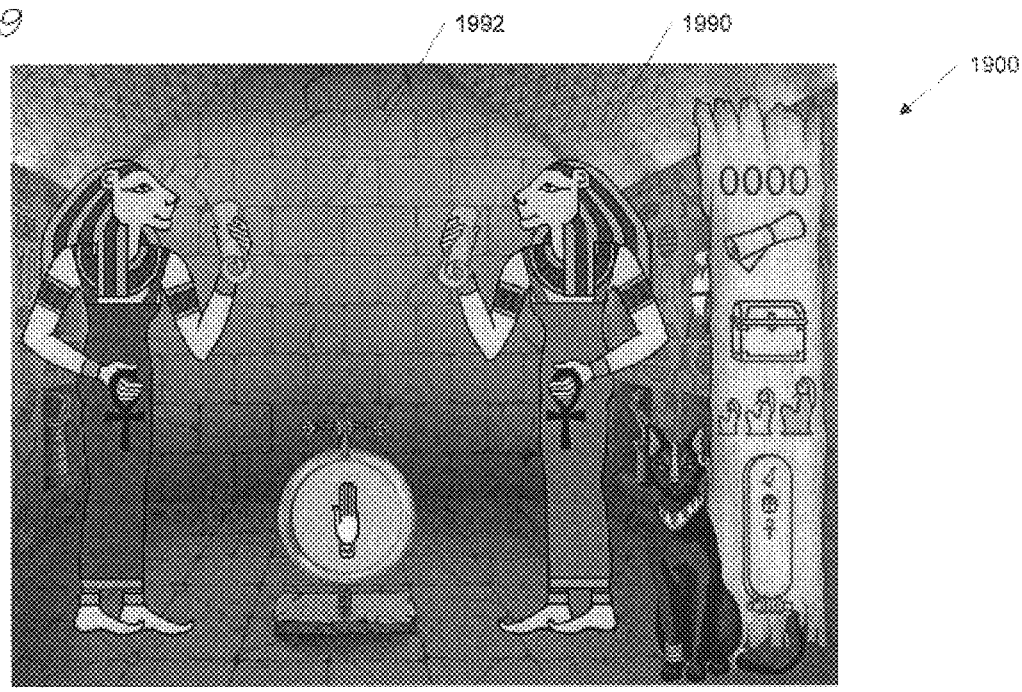
FIG. 19 is a pictorial representation of a screen in Treasure in the Tomb illustrating yet another game scene within the game.

Referring now to FIG. 19, a screen 1900 is shown. The screen 1900 illustrates the pharaoh's treasure room 1990, and includes the elements shown in FIG. 9. In addition, a wall of blocks 1992 are shown sealing off the entrance to the grave chamber of pharaoh phoneme. Reward animations are played for the subject, as described above, which remove the stones, one at a time, as the subject progresses through the trials. When the subject completes all necessary trials, the cartouche 1912 is updated to contain the special combination of hieroglyphics necessary to open the door of the tomb.

Figure 20:
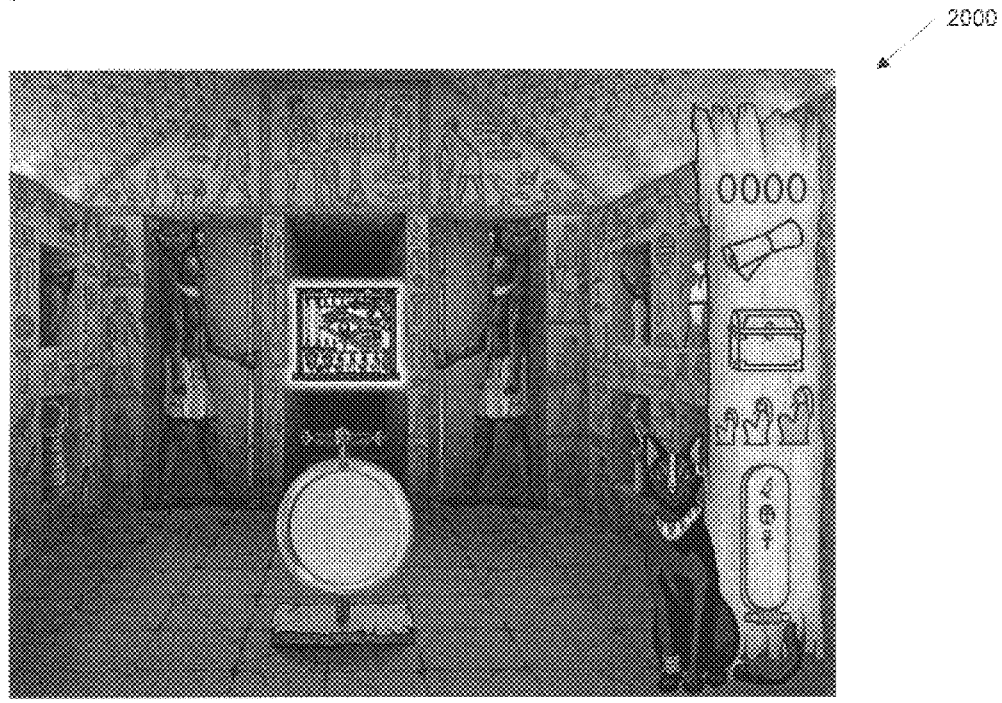
FIG. 20 is a pictorial representation of a screen in Treasure in the Tomb illustrating yet another game scene within the game.

Referring to FIG. 20, a screen 2000 is shown illustrating entrance into pharaoh phoneme's tomb. At this point, the subject has completed his/her progress through the game, and is rewarded with special animations.

With the above overview of the Treasure in the Tomb game, a detailed description of the methodology, and adaptive controls of the game will now be provided.

Stimulus Sets

In one embodiment, Treasure in the Tomb provides trials to train a subject to distinguish between the consonants—b, d, g, j, p, tk, c, m, n, s, and f, using ordered sets called "stimulus sets". Each stimulus set provides a target word, such as "bid", and up to three foil words, such as "did, kid, and lid". In this example, the stimulus set uses consonant-vowel-consonant (CVC) words to train the subject to recognize the initial consonant "b" of the target word "bid". Other stimulus sets are provided to test consonant discrimination in combination with other vowels, consonant discrimination at the end of words, and consonant discrimination in consonant-vowel-consonant-consonant (CVCC) words. A complete list of the stimulus sets used in Treasure in the Tomb are provided in Appendix A.

Stimulus Stages

For each stimulus set, there are 2 or 3 stages that are created. A stimulus stage is a pairing of a target and foil. In one embodiment, the first stage pairs the target with foil #3 in Appendix A. In general, this is the easiest pairing because it is the foil that is most different in terms of acoustic features from the target. As the subject progresses, s/he works toward stage 3 which pairs the target with foil #'1.

Display Phases

Within the Treasure in the Tomb game, there are two types of display modes, known as "Display Phases" in the game play. Phase I is similar to that described above with reference to FIGS. 9–21. In Phase I, upon initiation of a trial, a subject is presented with an auditory target word, and with its visual grapheme. The target word is played and the visual grapheme is presented briefly. The stimulus characters then present the pair target and foil. Upon correct selection of the target word, its associated grapheme is shown.

In Phase II, upon initiation of a trial, the target phoneme is presented auditorily only. That is, no associated grapheme is presented to the subject to assist him/her in identifying it from the foil.

Speech Processing

For each trial presented to a subject, the words within the stimulus stages may be processed to enhance the subject's ability to distinguish the target word from the distractor words. In one embodiment, Treasure in the Tomb provides 3 levels of speech processing for the target consonant portion of the target and foil words. Level 1 provides 20 dB of emphasis, without any time domain expansion. Level 2 provides 10 dB of emphasis, without any time domain expansion. Level 3 provides 0 dB of emphasis, without any time domain expansion (i.e., normal speech).

The emphasis uses an algorithm that differentially amplifies and disambiguates faster phonetic elements in speech. "Fast elements" in speech are defined as those that occur in the 3–30 Hz range within an envelope of narrow-band speech channels of a rate changed speech signal. An emphasis algorithm for these fast elements was implemented using two methods: a filter-bank summation method and an overlap-add method based on a short-time Fourier transform. Both of these emphasis algorithms, as well as other speech processing methods are fully described in co-pending U.S. patent application Ser. No. 08/982189, filed Dec. 17, 1997, entitled "METHOD AND APPARATUS FOR TRAINING OF SENSORY AND PERCEPTUAL SYSTEMS IN LLI SUBJECTS".

Having provided a description of the stimulus sets used for training, of the stimulus stages that are created, of the different phases of game play, and the speech processing used on the phonemes, a flow chart, as represented in FIG. 22, will now be described that illustrates the adaptive sequencing of Treasure in the Tomb thru all the sets, stages, phases and processing levels.

Figure 21A:
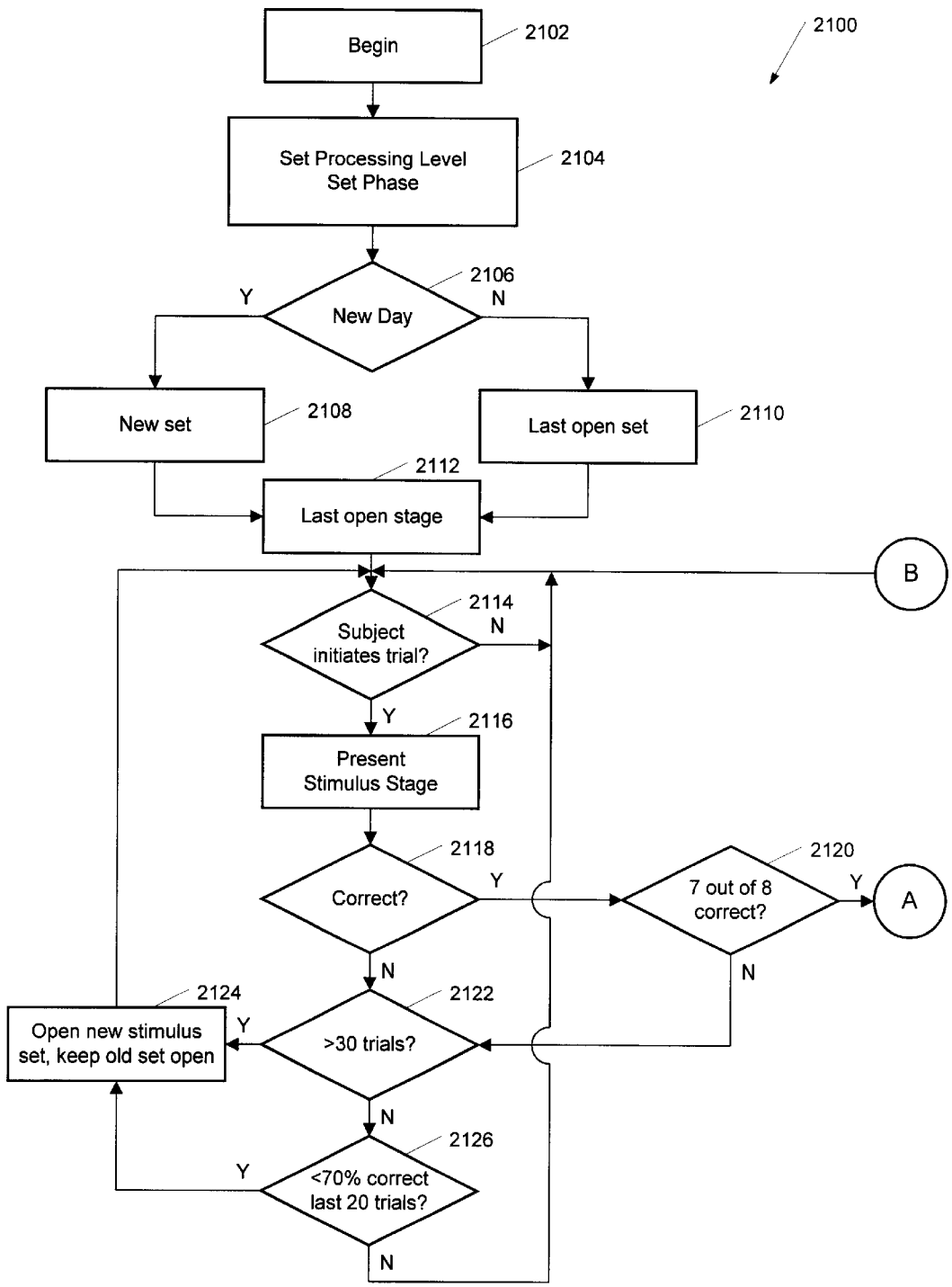
FIG. 21 is a pictorial representation of a screen in Treasure in the Tomb illustrating progression through the game scene of FIG. 20.
Figure 21B:
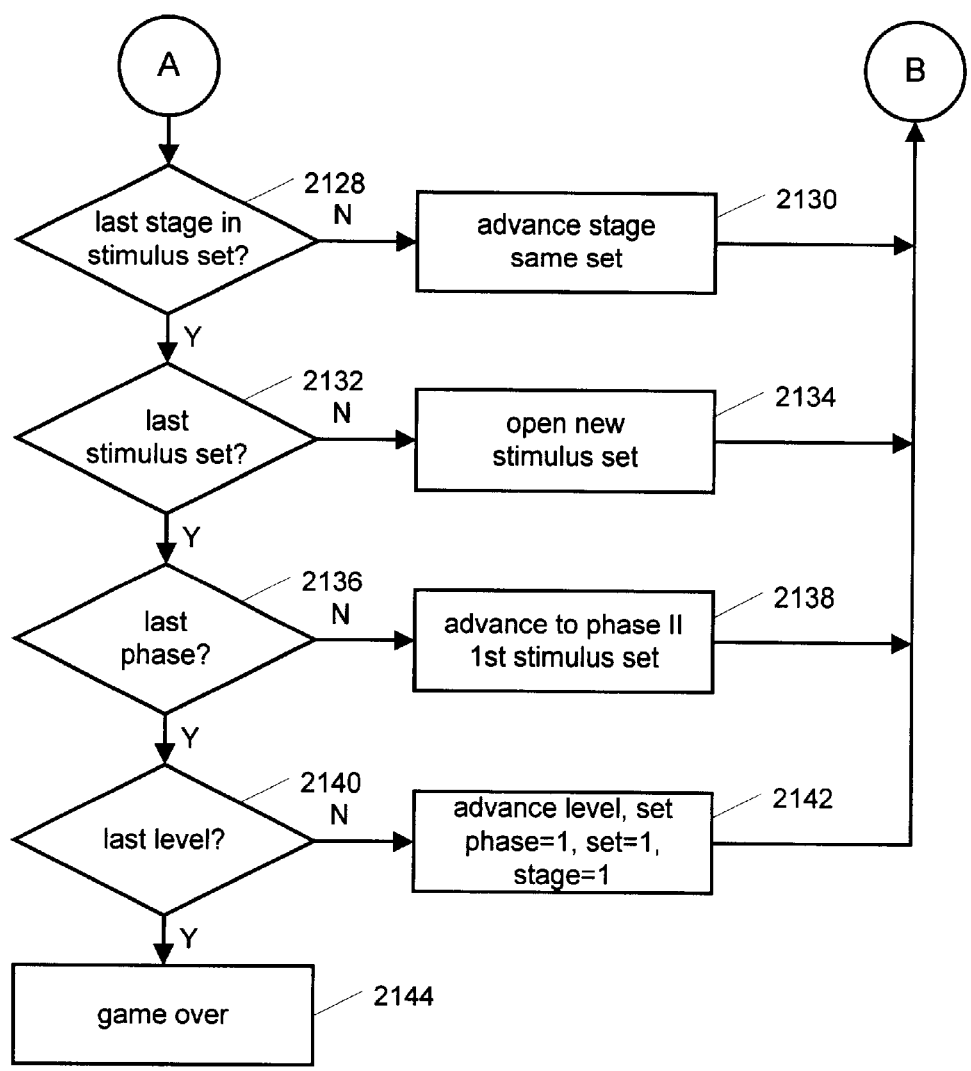

Referring to FIG. 21, a flow chart 2100 is shown illustrating the adaptive training methodology incorporated in the game Treasure in the Tomb. Game play begins at block 2102 and proceeds to block 2104.

At block 2104, the stimulus set is set equal to 1, the stage for the stimulus set is set equal to 1, the phase is set equal to 1, and the processing level is set equal to 1. Flow then proceeds to decision block 2106.

At decision block 2106, a determination is made as to whether the subject is re-entering the Treasure in the Tomb program on the same day, or whether this is the first entrance into the program this day. If it is a new day, flow proceeds to block 2108. Otherwise, flow proceeds to block 2110.

At block 2108, the stimulus set for testing is set to the next sequential, but previously unopened stimulus set. In one embodiment, there are 4 ways to change stimulus sets for testing. The first way is to get 7 out of 8 trials correct in the last stage of the current stimulus set. When this happens, the current stimulus set is closed, and the next sequential set is opened. The second way is to maintain less than 70% correct over 20 trials at any stage. When this occurs, the current stimulus set is kept open (for later testing), and the next sequential stimulus set is opened. The third way is to perform more than 30 trials at any stage. When this occurs, the current stimulus set is left open, and the next sequential stimulus set is selected. The fourth way is to begin a new day. In this instance, the previous days stimulus set is kept open, but the next sequential stimulus set is selected. Flow then proceeds to block 2112.

At block 2110, the last open stimulus set is selected. That is, the stimulus set that was being tested on prior to the game being interrupted, will be selected for testing. Flow then proceeds to block 2112.

At block 2112, the last open stimulus stage for the selected stimulus set is selected. Recall, for each stimulus set, 2–3 stages are provided for testing. For example, if the stimulus set that is open is stimulus set #5 (see Appendix A), and the stage is #2, the subject is being tested on a target phoneme of "bud", against a foil of "cud". Flow then proceeds to decision block 2114.

At decision block 2114, a determination is made as to whether the subject has initiated a trial. Recall, a subject initiates a trial by pressing a button on a computer mouse, while placing the cursor over the gong 940. If the subject has not initiated a trial, flow continues at decision block 2114. Otherwise, flow proceeds to block 2116.

At block 2116, a trial is presented using the current stimulus set, at the current stage. Flow then proceeds to decision block 2118.

At decision block 2118, a determination is made as to whether the subject has correctly responded to the trial. Recall, a correct response is provided when the subject distinguishes between a target phoneme and a foil, and selects the stimulus character 930 that presented the target phoneme. If the subject is correct, flow proceeds to decision block 2120. Otherwise, flow proceeds to decision block 2122.

At decision block 2120, a determination is made as to whether the subject has correctly responded to 7 out of the last 8 trials, on a sliding scale. If not, then flow proceeds to decision block 2122. Otherwise, flow proceeds to decision block 2128.

At decision block 2122, a determination is made as to whether the subject has been tested more than 30 times within the current stimulus set, and current stimulus stage. If so, flow proceeds to block 2124. Otherwise, flow proceeds to decision block 2126.

At block 2124, the subject has reached this block because s/he has been unable to get 7 out of 8 correct, for a given stimulus set, and a given stimulus stage, in more than 30 trials. Rather than continuing to test the current stimulus set, a new stimulus set is selected for testing. However, the program records the stimulus set and stimulus stage that has not yet been completed, and leaves this set open for later testing. The subject will not be allowed to progress to the next phase, or the next processing level until completing this stimulus set. Flow then proceeds back to decision block 2114 to await initiation of another trial.

At decision block 2126, a determination is made as to whether the subject has responded correctly to less than 70% of the trials, over the last 20 trials. If this is the case, flow proceeds to block 2124 for selection of another stimulus set. Otherwise, flow proceeds back to decision block 2114 to await another trial.

At decision block 2128, a determination is made as to whether the subject has responded correctly to 7 out of the last 8 trials, in the last stage of a stimulus set. That is, the subject has reached decision block 2128 by correctly responding to 7 out of the last 8 trials. Now, a determination is made as to whether the correct responses were within the last stage of a stimulus set. If not, then flow proceeds to block 2130. Otherwise, flow proceeds to decision block 2132.

At block 2130, the next stimulus stage for the current stimulus set is selected for testing. In addition, the current stimulus stage is closed. The subject will not see the current stimulus stage, at the current phase and processing level, anymore. This is because the subject has sufficiently distinguished between the target phoneme, and a particular foil, that no further testing is necessary. Flow then proceeds back to decision block 2114 to await initiation of another trial.

At decision block 2132, a determination is made as to whether the subject has correctly completed all of the stimulus sets. If not, flow proceeds to block 2134. Otherwise, flow proceeds to decision block 2136.

At block 2134, the current stimulus set is closed, and the next sequential stimulus set is opened, beginning at stage 1. Recall, if the subject previously switched out of a stimulus set prior to closing it out, that stimulus set remains open. Block 2134 insures that all open stimulus sets are cycled through before a new phase can be started. Flow then proceeds back to decision block 2114 to await initiation of another trial.

At decision block 2136, a determination is made as to whether the subject has completed the last phase. That is, given two phases, and beginning at phase I, has the subject just completed phase II? If not, flow proceeds to block 2138. Otherwise, flow proceeds to decision block 2140.

At block 2138, all stimulus sets within phase I are closed, and the current stimulus set is reset to set=1, stage=1. Flow then proceeds back to decision block 2114 to await initiation of another trial.

At decision block 2140, a determination is made as to whether the current processing level is the last level. That is, given processing levels 1–3, is the subject's current processing level, level 3? If not, flow proceeds to block 2142. Otherwise, flow proceeds to block 2144.

At block 2142, the subject has successfully completed both phases, for all stages, for all stimulus sets, at a given processing level. The level is therefore advanced, and the phase, set, and stage are set equal to 1. Flow then proceeds back to decision block 2114 to await initiation of another trial.

At block 2144, the subject has correctly responded to 7 out of 8 trials, for each stage of each stimulus set, in each phase, for each processing level. At this point, the Treasure in the Tomb game is completed.

The flow chart 2100 thus describes a particular embodiment of the present invention for adaptively training a subject to distinguish between similar sounding words, whether the target phoneme is in the front, middle or end of a word, and to associate particular words with their representative graphemes.

Although the present invention and its objects, features, and advantages have been described in detail, other embodiments are encompassed by the invention. For example, the methodology of the present invention has been described with reference to a particular game story entitled Treasure in the Tomb. It should be appreciated that the story line for the game is inconsequential to the methodology used to train a subject in word/grapheme recognition. While the story line of the game should be engaging and entertaining, other story lines, game scenarios, etc., could be used.

In addition, a particular strategy has been shown in FIG. 21 for adaptively altering stimulus sets, stages, processing levels, etc., based on a subject's performance. Other performance criteria could be used to modify trial sequencing, without departing from the training methodology encompassed by the present invention.

Furthermore, the stimulus sets shown in Appendix A are not exhaustive. Rather, it is believed that they provide significant training for a subject, given particular time constraints on game play imposed by the market. However, additional or alternative stimulus sets are anticipated by the inventors.

Moreover, only 3 speech processing levels have been described for enhancing word recognition. It should be appreciated that additional or alternative speech processing could be used to further enhance a subject's neurological training. Such speech processing could include time expansion, as well as frequency component emphasis, of selected words, and could include varying the Inter-Stimulus-Interval between presented words.

Finally, the Treasure in the Tomb program has been shown for execution on a personal computer connected to a central server. However, as technology advances, it is envisioned that the program could be executed either by a diskless computer attached to a server, by a handheld processing device, such as a laptop, or eventually by a palmtop device such as a Nintendo GameBoy. As long as the graphical images and auditory prompts can be presented in a timely fashion, and with high quality, the nature of the device used to present the material is irrelevant.

Those skilled in the art should appreciate that they can readily use the disclosed conception and specific embodiments as a basis for designing or modifying other structures for carrying out the same purposes of the present invention without departing from the spirit and scope of the invention as defined by the appended claims.

APPENDIX A

|  | target | foil #1 | foil #2 | foil #3 |
|---|---|---|---|---|
| Initial change | | | | |
| B's with different vowels | | | | |
| 1 | bid | did | kid | lid |
| 2 | bit | pit | kit | hit |
| 3 | bag | tag | gag | nag |
| 4 | bet | pet | get | wet |
| 5 | bud | dud | cud | mud |
| 6 | bob | cob | sob | job |
| D's with different vowels | | | | |
| 7 | did | bid | rid | hid |
| 8 | dip | tip | lip | sip |
| 9 | dad | bad | pad | had |
| 10 | dud | bud | mud | sud |
| 11 | dog | bog | fog | log |
| G's with different vowels | | | | |
| 12 | get | bet | set | net |
| 13 | gag | bag | lag | sag |
| 14 | god | pod | nod | rod |
| 15 | gut | but | rut | hut |
| G's with different vowels | | | | |
| 16 | pip | dip | hip | sip |
| 17 | pad | bad | dad | sad |
| 18 | peg | beg | keg | leg |
| 19 | pod | god | cod | mod |
| 20 | pot | dot | lot | rot |
| 21 | pug | bug | dug | hug |
| T's with different vowels | | | | |
| 22 | tab | cab | lab | dab |
| 23 | tag | bag | gag | wag |
| 24 | ted | bed | wed | fed |
| 25 | tub | dub | pub | rub |
| K's with different vowels | | | | |
| 26 | kid | did | bid | lid |
| 27 | keg | peg | beg | leg |
| C's with different vowels | | | | |
| 28 | cap | gap | map | nap |
| 29 | cob | gob | rob | job |
| 30 | cop | top | mop | hop |
| 31 | cub | tub | rub | hub |
| CVCCs onset change, rhyme constant | | | | |
| CK | | | | |
| 32 | buck | duck | tuck | luck |
| 33 | sick | pick | tick | kick |
| 34 | duck | buck | puck | suck |
| 35 | peck | deck | neck | heck |
| 36 | pock | dock | rock | lock |
| 37 | tack | pack | back | sack |
| 38 | tock | dock | sock | lock |
| 39 | kick | tick | pick | sick |
| SH | | | | |
| 40 | bush | push | tush | |
| 41 | dish | pish | wish | fish |
| 42 | cash | dash | mash | rash |

APPENDIX A-continued

| | target | foil #1 | foil #2 | foil #3 |
|---|---|---|---|---|
| ST | | | | |
| 43 | bust | dust | just | must |
| 44 | gist | fist | list | mist |
| 45 | past | cast | mast | last |
| 46 | post | most | host | |
| 47 | cast | past | last | fast |
| Final Change | | | | |
| B's with different vowels | | | | |
| 48 | bad | bat | bag | bath |
| 49 | bud | but | bug | buck |
| D's with different vowels | | | | |
| 50 | did | dig | dip | dish |
| 51 | dub | dud | dug | duck |
| G | | | | |
| 52 | got | god | gob | gosh |
| P's with different vowels | | | | |
| 53 | pad | pat | pan | path |
| 54 | pig | pit | pin | pick |
| 55 | pup | pug | pun | puck |
| T's with different vowels | | | | |
| 56 | tip | tim | tin | tick |
| 57 | tub | tug | tum | tuck |
| K | | | | |
| 55 | kid | kit | kim | kick |
| C | | | | |
| 59 | cob | cod | cot | cop |

What is claimed is:

1. A method for adaptively training a human subject, within the context of an animated game, to distinguish between an auditorily presented acoustically processed target phoneme and a foil phoneme, and to associate the target phoneme with a corresponding grapheme, the method comprising:
   a) presenting the acoustically processed target phoneme to the human subject;
   b) subsequent to presenting the acoustically processed target phoneme to the human subject, presenting the acoustically processed target phoneme and its corresponding grapheme, and the foil phoneme and its corresponding grapheme, the target and foil phonemes presented in either target-foil or foil-target order;
   c) detecting whether the human subject indicated selection of the acoustically processed target phoneme, or the foil phoneme;
   d) recording the human subject's selection;
   e) repeating a)–d); and
   f) after correct selection of a plurality of processed target phonemes by the human subject, altering the acoustically processing applied to the target and foil phonemes.

2. The method for adaptively training a human subject, as recited in claim 1, wherein the auditorily presented target phoneme and foil phoneme is consonant-vowel-consonant (CVC) or consonant-vowel-consonant-consonant (CVCC) constructs.

3. The method for adaptively training a human subject, as recited in claim 1, wherein the corresponding grapheme comprises a visual image of the target phoneme.

4. The method for adaptively training a human subject, as recited in claim 2, wherein the acoustic processing of the target and foil phonemes selectively amplifies particular frequency envelopes within a consonant portion of the phonemes.

5. The method for adaptively training a human subject, as recited in claim 4, wherein a plurality of amplification levels is provided.

6. The method for adaptively training a human subject, as recited in claim 5, wherein the amplification levels include 20 db, 10 db and 0 db.

7. The method for adaptively training a human subject, as recited in claim 1, wherein steps a) and b) present the target and foil phonemes by acoustically playing the phonemes through a speaker.

8. The method for adaptively training a human subject, as recited in claim 7, wherein the speaker comprises headphones.

9. The method for adaptively training a human subject, as recited in claim 7, wherein steps a) and b) present the corresponding graphemes on a visual display, simultaneously with acoustically playing the phonemes.

10. The method for adaptively training a human subject, as recited in claim 1, wherein a) further comprises:
    i) selecting the processed target phoneme from a set of possible target phonemes; and
    ii) selecting the processed foil phoneme from a set of possible foil phonemes associated with the selected processed target phoneme.

11. The method for adaptively training a human subject, as recited in claim 1, wherein a) further comprises:
    i) associating a first graphic image with the target phoneme and a second graphic image with the foil phoneme; and
    ii) animating each of the first and second graphic images as their associated phoneme is presented.

12. The method for adaptively training a human subject, as recited in claim 11, wherein the human subject indicates selection of the processed target phoneme by selecting the first graphic image.

13. The method for adaptively training a human subject, as recited in claim 12, wherein the human subject selects the first graphic image by moving a cursor over the first graphic image, and pressing a button on a mouse.

14. The method for adaptively training a human subject, as recited in claim 1, wherein c) is repeated a predetermined number of times prior to d).

15. The method for adaptively training a human subject, as recited in claim 1, wherein step f) further comprises:
    i) after correct selection of a first plurality of processed target phonemes, changing the foil phoneme presented with the target phoneme.

16. The method for adaptively training a human subject, as recited in claim 15, wherein step f) further comprises:
    i) after correct selection of a second plurality of processed target phonemes, changing the target phoneme that is presented.

17. The method for adaptively training a human subject, as recited in claim 16, wherein step f) further comprises:
    iii) after correct selection of a third plurality of processed target phonemes, changing the acoustically processing applied to the target and foil phonemes.

18. The method for adaptively training a human subject, as recited in claim 17, wherein the acoustically processing applied to the target and foil phonemes emphasizes selected frequency envelopes of the phonemes 20 db, 10 db or 0 db.

19. The method for adaptively training a human subject, as recited in claim 18, wherein step iii) reduces the emphasis applied to the target and foil phonemes.

* * * * *